(12) United States Patent
Arab et al.

(10) Patent No.: US 11,098,351 B2
(45) Date of Patent: Aug. 24, 2021

(54) APPARATUS AND METHODS FOR MULTI-STEP CHANNEL EMULSIFICATION

(71) Applicant: LUMINEX CORPORATION, Austin, TX (US)

(72) Inventors: Nicolas Arab, Austin, TX (US); Arnold Estrada, Austin, TX (US); Daniel Fine, Austin, TX (US); Ross Johnson, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 0 days.

(21) Appl. No.: 16/858,913

(22) Filed: Apr. 27, 2020

(65) Prior Publication Data

US 2020/0263237 A1    Aug. 20, 2020

Related U.S. Application Data

(63) Continuation of application No. 15/070,108, filed on Mar. 15, 2016, now Pat. No. 10,662,470.

(60) Provisional application No. 62/269,289, filed on Dec. 18, 2015, provisional application No. 62/133,621, filed on Mar. 16, 2015.

(51) Int. Cl.
*B01F 13/00* (2006.01)
*B01F 3/08* (2006.01)
*C12Q 1/686* (2018.01)
*B01L 7/00* (2006.01)
*B01L 3/00* (2006.01)

(52) U.S. Cl.
CPC ............ *C12Q 1/686* (2013.01); *B01F 3/0807* (2013.01); *B01F 3/0865* (2013.01); *B01F 13/0059* (2013.01); *B01F 13/0064* (2013.01); *B01F 2215/0037* (2013.01); *B01L 3/502784* (2013.01); *B01L 7/52* (2013.01)

(58) Field of Classification Search
None
See application file for complete search history.

(56) References Cited

U.S. PATENT DOCUMENTS

| 3,457,336 | A | | 7/1969 | Harris |
| 3,713,780 | A | * | 1/1973 | Shapiro ................... B01L 3/502 422/413 |
| 5,455,315 | A | | 10/1995 | Paine et al. |
| 5,938,581 | A | | 8/1999 | Bibette et al. |

(Continued)

OTHER PUBLICATIONS

Dangla, et al., "Droplet microfluidics driven by gradients of confinement," *PNAS*, 110:853-8, 2013.

(Continued)

*Primary Examiner* — Brian R Gordon
(74) *Attorney, Agent, or Firm* — Parker Highlander PLLC

(57) ABSTRACT

Methods and devices for forming droplets are provided. In certain embodiments, the methods and devices form droplets having different diameters. In particular embodiments, the device includes a fluid supply channel, a collection chamber, and one or more nozzles disposed between the fluid supply channel and the collection chamber. Each nozzle may include an inlet portion with a channel height, a first step with a first step height and a first tread length, and a second step with a second step height and a second tread length. In certain embodiments, the first step height is greater than the channel height, and the second step height is greater than the first step height.

20 Claims, 11 Drawing Sheets

(56) References Cited

U.S. PATENT DOCUMENTS

| | | | |
|---|---|---|---|
| 7,943,671 B2 | 5/2011 | Herminghaus et al. | |
| 7,993,908 B2* | 8/2011 | Hvichia | B01D 35/30 |
| | | | 435/287.2 |
| 9,216,413 B2* | 12/2015 | Blankenstein | B01L 3/502753 |
| 9,861,983 B2* | 1/2018 | Hvichia | G01N 33/491 |
| 2005/0167370 A1 | 8/2005 | Nakajima et al. | |
| 2009/0285720 A1* | 11/2009 | Shinoda | B01L 3/5027 |
| | | | 422/82.05 |
| 2009/0312442 A1 | 12/2009 | Herminghaus | |
| 2011/0217712 A1 | 9/2011 | Hiddessen et al. | |
| 2011/0236277 A1* | 9/2011 | Lee | B29C 33/3878 |
| | | | 422/506 |
| 2012/0315203 A1 | 12/2012 | Baroud et al. | |
| 2012/0322162 A1 | 12/2012 | Collier et al. | |
| 2012/0329038 A1 | 12/2012 | Ismagilov et al. | |
| 2013/0078164 A1 | 3/2013 | Baroud et al. | |
| 2014/0024023 A1 | 1/2014 | Cauley, III et al. | |
| 2014/0271909 A1* | 9/2014 | Hvichia | B01L 3/502753 |
| | | | 424/529 |
| 2015/0034163 A1 | 2/2015 | Abate et al. | |
| 2015/0355072 A1* | 12/2015 | Hayden | B03C 1/01 |
| | | | 435/7.2 |
| 2018/0003632 A1* | 1/2018 | Wei | B01L 3/502715 |
| 2019/0099751 A1* | 4/2019 | Hyun | B01F 5/0475 |
| 2019/0314819 A1* | 10/2019 | Johnson | C12Q 1/18 |
| 2020/0290048 A1* | 9/2020 | Bharadwaj | B01L 3/0241 |
| 2020/0378961 A1* | 12/2020 | Schnall-Levin | |
| | | | G01N 33/54313 |
| 2021/0031189 A1* | 2/2021 | Johnson | B01L 3/502784 |

OTHER PUBLICATIONS

Extended European Search Report issued in corresponding European Application No. 16765576.0, dated Oct. 19, 2018.

International Search Report and Written Opinion issued in PCT/US2016/022418, dated Jul. 29, 2016.

Invitation to Pay Additional Fees issued in PCT/US2016/022418, dated May 5, 2016.

Kreutz, et al., "Theoretical design and analysis of multivolume digital assays with wide dynamic range validated experimentally with microfluidic digital PCR," *Analytical Chemistry*, 83:8158-68, 2011.

Link, et al., "Geometrically mediated breakup of drops in microfluidic devices," *Phys. Rev. Lett.*, 92:054503, 2004.

Office Communication issued in U.S. Appl. No. 15/070,108, dated Feb. 1, 2018.

Office Communication issued in U.S. Appl. No. 15/070,108, dated Jun. 18, 2018.

Seemann, et al., "Droplet based microfluidics" *Rep. Prog. Phys.*, 75: 016601, 2012.

Sugiura, et al., "Interfacial tension driven monodispersed droplet formation from microfabricated channel array," *Langmuir*, 17:5562-6, 2001.

Thorsen, et al., "Dynamic pattern formation in a vesicle-generating microfluidic device," *Phys. Rev. Lett.*, 86:4163-6, 2001.

* cited by examiner

APPARATUS AND METHODS FOR MULTI-STEP CHANNEL EMULSIFICATION

CROSS-REFERENCE TO RELATED APPLICATIONS

This application is a continuation of U.S. patent application Ser. No. 15/070,108, filed Mar. 15, 2016, which claims priority to U.S. Provisional Patent Application Serial Nos. 62/133,621 filed Mar. 16, 2015 and 62/269,289 filed Dec. 18, 2015, the contents of each of which are incorporated herein by reference.

FIELD OF THE INVENTION

Embodiments of the present invention relate to methods and devices for forming droplets.

BACKGROUND

The following descriptions and examples are not admitted to be prior art by virtue of their inclusion within this section.

Compartmentalization is a technique that is becoming increasingly popular in the molecular diagnostics and life science research fields. Applications include digital polymerase chain reaction (PCR), two-stage PCR multiplexing (including genotyping), single-cell analysis, targeted sequencing, multiplex immunoassays, ultra-sensitive immunoassays, and library prep for sequencing. Each separate application places different demands on the number of compartments, monodispersity of each compartment, and the volume of each compartment.

One approach for compartmentalizing reactions is by using droplets, which are isolated volumes of a first fluid that are completely surrounded by a second fluid or by a second fluid and one or more surfaces. In the molecular diagnostics and life science research fields this is typically two immiscible liquids. Techniques for droplet generation include co-flow, flow focusing, and T-junction. Co-flow droplet generation forms droplets via pinching of the inner flow from an orifice in a co-flow design as described by, for example, David Weitz ("Monodisperse emulsion generation via drop break off in a coflowing stream," Langmuir, 2000). Stone and Weitz ("Monodisperse double emulsions generated from a microcapillary device," Science, 2005) demonstrated double emulsions using a modified co-flowing technique. Flow focusing uses a co-flow design which is geometrically confined in the channel to produce droplets (see, e.g., Stone, "Formation of dispersions using "flow focusing" in microchannels," APL, 2003). T-junction droplet generation methods and modifications thereof (e.g., Y-junction, cross junction, ψ-junction) generally involve intersecting flows of continuous and dispersed phases (see, e.g., Quake, "Dynamic pattern formation in a vesicle-generating microfluidic device", PRL, 2001; and Weitz, D. A., Stone, H., "Geometrically mediated breakup of drops in microfluidic devices," PRL, 2004). Additionally, U.S. Pat. No. 7,943,671 (incorporated herein by reference) described a step emulsification technique that employed an abrupt change in the aspect ratio of a single microchannel to rapidly destabilize a confined co-flowing stream.

The droplet generation techniques described above all require flows of both continuous and dispersed phases. In contrast, Sugiura et al. described a technique in which droplet formation was driven largely by interfacial tension (Sugiura, S., Nakajima, M. "Interfacial tension driven monodispersed droplet formation from microfabricated channel array," Langmuir, 17:5562-5566 (2001)). With this technique, droplets are generated via falling off a ledge after ejection from a fluidic channel. More recently, Dangla et al., have also described techniques for generating droplets by modulating the interfacial curvature between immiscible liquids using a sloped ceiling to produce a continuously increasing gap height, called a gradient of confinement (U.S. Pat. Pub. 2013/0078164 (incorporated herein by reference); Dangla et al., "Droplet microfluidics driven by gradients of confinement," PNAS, 10(3):853-858 (2013)). This gradient of confinement has similarities with the interfacial curvature modulation achieved with a discrete step as described by Sugiura et al. (see above).

SUMMARY OF THE INVENTION

Exemplary embodiments of the present disclosure relate to systems and methods for forming droplets, including a multi-step microchannel emulsification device.

One embodiment provides an emulsification device comprising: a channel having an inlet portion; a first step in fluid communication with the inlet portion; a second step in fluid communication with the first step; and a third step in fluid communication with the second step. In some embodiments, the emulsification device comprises a plurality of inlet portions, a single continuous first step or a plurality of first steps that are each in fluid communication with an inlet portion in the plurality of inlet portions; a single continuous second step or a plurality of second steps that are each in fluid communication with either the single continuous first step or a first step in the plurality of first steps, and a single continuous third step or a plurality of third steps that are each in fluid communication with the single second step or a second step in the plurality of second steps.

The channel having the inlet portion has a channel height CH and a width CW. In certain embodiments, CW is greater than CH, while in other embodiments CH is greater than CW. In particular embodiments, the ratio of CW/CH is between 0.1 to 10.0, 0.2 to 8.0, 0.5 to 5.0, 1.0 to 4.0, 2.0 to 4.0, or 2.5 to 3.5. In certain embodiments, the ratio of CW/CH is about 3.0.

Specific embodiments include a first step in fluid communication with the inlet portion, where the first step has a tread length T1 and a step height SH1. In certain embodiments, SH1 is greater than CH by a riser height R1, where R1 is greater than zero. In specific embodiments, the ratio of SH1/CH is greater than 1.0 and less than 10.0, or more particularly greater than 1.0 and less than 5.0, or more particularly greater than 1.0 and less than 4.0, or more particularly still greater than 1.0 and less than 2.0. In particular embodiments, the ratio of SH1/CH is approximately 1.5. Specific embodiments include a second step in fluid communication with the first step, where the second step has a tread length T2 and a step height SH2. In particular embodiments, SH2 is greater than SH1 by a riser height R2, where R2 is greater than zero. In certain embodiments, the ratio of SH2/CH is greater than 1.0 and less than 10.0, or more particularly greater than 1.0 and less than 5.0, or more particularly greater than 1.0 and less than 3.0. In particular embodiments, the ratio of SH2/CH is approximately 2.0. Particular embodiments include a third step in fluid communication with the second step, where the third step has a step height SH3 that is greater than SH2 by a riser height R3, where R3 is greater than zero. In certain embodiments, the ratio of SH3/CH is greater than 1.0 and less than 15.0, or more particularly greater than 1.0 and less than 10.0, or more particularly greater than 5.0 and less than 10.0. In particular embodiments, the ratio of SH3/CH is approximately 7.5.

In particular embodiments, R1 is greater than 0.1 micron and less than 1000 microns, greater than 1.0 micron and less than 100 microns, greater than 5.0 microns and less than 100 microns, greater than 5.0 microns and less than 50 microns, greater than 1.0 micron and less than 50 microns, greater than 1.0 micron and less than 20 microns, greater than 3.0 microns and less than 30 microns, or greater than 5.0 microns and less than 20.0 microns. In certain embodiments, R1 is at least 5.0 microns. In some embodiments, R1 is about 5, 10, or 20 microns, or any range derivable therein. In particular embodiments, R2 is greater than 0.1 micron and less than 1000 microns, greater than 1.0 micron and less than 100 microns, greater than 5.0 microns and less than 100 microns, greater than 5.0 microns and less than 50 microns, greater than 1.0 micron and less than 50 microns, greater than 1.0 micron and less than 20 microns, greater than 3.0 microns and less than 30 microns, or greater than 5.0 microns and less than 20.0 microns. In certain embodiments, R2 is at least 5.0 microns. In some embodiments, R2 is about 5, 10, or 20 microns, or any range derivable therein. In some embodiments, R1 is equal to R2. In particular embodiments, R3 is greater than 0.1 micron and less than 1000 microns, greater than 1.0 micron and less than 1000 microns, greater than 5.0 microns and less than 1000 microns, greater than 5.0 microns and less than 500 microns, greater than 10.0 microns and less than 1000 microns, greater than 10.0 micron and less than 500 microns, greater than 50 microns and less than 300 microns, or greater than 100.0 microns and less than 1000.0 microns. In some embodiments, R3 is about 55, 110, or 275 microns, or any range derivable therein. In certain embodiments, R3 is at least 55.0 microns. In certain embodiments, R3 is at least 275 microns. In particular embodiments configured to produce different size droplets, CH will be 10 microns, 20 microns, and 50 microns, and R1 will equal R2 and will be 5 microns, 10 microns, and 25 microns. In certain embodiments configured to produce different size droplets, R3 will be 55 microns, 110 microns and greater than 275 microns. In some embodiments, R1 is greater than R2, and R2 is greater than R3. In other embodiments, R3 is greater than, R2, and R2 is greater than R1. In some embodiments, R1=R2=R3. In yet other embodiments, R1=R2, and R3 is greater than R1. In some embodiments, the ratio of R3/R1 is at least 10.0. In some embodiments, the ratio of R3/R2 is at least 10.0.

In specific embodiments, the ratio of T1/CH is between 0.1 and 7, or more particularly greater 1 and less than 5, or more particularly greater than 3.0 and less than 4.0. In certain embodiments, the ratio of T1/CH is greater than 1.0. In specific embodiments, the ratio of T2/CH is between 0.1 and 7, or more particularly greater 1 and less than 5, or more particularly greater than 3.0 and less than 4.0. In certain embodiments, the ratio of T2/CH is greater than 1.0. In certain embodiments the ratio of T2/CH is less than T1/CH.

In certain embodiments of the emulsification device, CH is between 1 micron and 50 microns, or more particularly between 5 microns and 30 microns, or more particularly between 6 and 20 microns, or more particularly between 8 and 12 microns, or still more particularly approximately 10 microns. In certain embodiments, CH is at least 5 microns, 10 microns, 20 microns, or 50 microns.

In particular embodiments, the first step has a width W1 greater than CW, the second step has a width W2 greater than CW, and the third step has a width W3 that is greater than CW. In certain embodiments, the first step has a width W1 greater than CW, the second step has a width W2 equal to W1, and the third step has a width W3 that is greater than W1. In certain embodiments, W1=W2=W3. Particular embodiments include a plurality of inlet portions, where each inlet portion in the first plurality of inlet portions has a height CH and a width CW. In certain embodiments, the ratio of CW/CH is greater 1.0 for each inlet portion. In certain embodiments, the ratio of CW/CH is between 0.1 to 10.0, 0.2 to 8.0, 0.5 to 5.0, 1.0 to 4.0, 2.0 to 4.0, or 2.5 to 3.5 for each inlet portion. In certain embodiments, the ratio of CW/CH is about 3.0 for each inlet portion. Certain embodiments include a plurality of first steps, wherein each first step in the plurality of first steps is in fluid communication with an inlet portion in the plurality of inlet portions, and has a length T1 and a height SH1, where SH1 is greater than CH by a riser height R1. Some embodiments include a continuous first step in fluid communication with the inlet portions in the plurality of inlet portions, and have a length T1 and a height SH1, where SH1 is greater than CH by a riser height R1. In particular embodiments, the ratio of SH1/CH is greater than 1.0. In specific embodiments, the ratio of SH1/CH is greater than 1.0 and less than 10.0, or more particularly greater than 1.0 and less than 5.0, or more particularly greater than 1.0 and less than 4.0, or more particularly still greater than 1.0 and less than 2.0. In particular embodiments, the ratio of SH1/CH is approximately 1.5. Particular embodiments include a plurality of second steps, where each second step in the plurality of second steps is in fluid communication with a first step in the plurality of first steps or a single continuous first step, is in fluid communication with the third step, and has a length T2 and a height SH2, where SH2 is greater than SH1 by a riser height R2. Some embodiments include a single continuous second step in fluid communication with the single continuous first step or the plurality of first steps, is in fluid communication with the third step, and has a length T2 and a height SH2, where SH2 is greater than SH1 by a riser height R2. In particular embodiments, the ratio of SH2/CH is greater than 1.0. In certain embodiments, the ratio of SH2/CH is greater than 1.0 and less than 10.0, or more particularly greater than 1.0 and less than 5.0, or more particularly greater than 1.0 and less than 3.0. In particular embodiments, the ratio of SH2/CH is approximately 2.0. In some embodiments, the single continuous second step or plurality of second steps is in fluid communication with a common third step. Other embodiments include a plurality of third steps, where each third step is in fluid communication with a single continuous second step or a second step of a plurality of second steps.

In some embodiments, the emulsification device has a single inlet portion. In other embodiments, the emulsification device has a plurality of inlet portions. In specific embodiments, the emulsification device has 2, 3, 4, 5, 6, 7, 8, 9, 10, 20, 30, 40, 50, 60, 70, 80, 90, 100, 150, 200, 250, 500, or 1000 inlet portions, or any range derivable therein. The plurality of inlet portion may each be in fluid communication with one or more of a dedicated first, second, and/or third step in a plurality of first, second, and/or third steps or the plurality of inlet portions may be in fluid communication with one or more of a common first, second, and/or third step.

In some embodiments, the emulsification device has a single nozzle. In other embodiments, the emulsification device has a plurality of nozzles. In specific embodiments, the emulsification device has 2, 3, 4, 5, 6, 7, 8, 9, 10, 20, 30, 40, 50, 60, 70, 80, 90, 100, 150, 200, 250, 500, or 1000 nozzles, or any range derivable therein. The plurality of nozzles may each be in fluid communication with a dedicated third step in a plurality of third steps or the plurality of nozzles may be in fluid communication with a common third step. Two or more nozzles of the plurality of nozzles may have geometries configured to form droplets of two or more different sizes. For example, an emulsion device may have three populations of nozzles or channels in which a first population has the geometries CH=10 microns, R1=5 microns, R2=5 microns, a second population has the geometries CH=20 microns, R1=10 microns, R2=10 microns, and a third population has the geometries CH=50 microns, R1=25 microns, R2=25 microns, whereby the first, second, and third populations of nozzles produce droplets of about 45 microns, 120 microns, and 300 microns, respectively. The various sized droplets may be collected in a common third step region or the various sized droplets may be collected in separate third step regions with other droplets of the same size. Where the device contains a plurality of spatially separated third step regions, each third step may have a riser height R3 and or step height SH3 that is different from one or more of the other third step regions. By way of illustration, in the example discussed above with droplets of about 45 microns, 120 microns, and 300 microns, the value of R3 for three distinct third step regions could be 55 microns, 110 microns, and 275 microns.

Certain embodiments include a method of forming an emulsion using an emulsification device according to the present disclosure. In particular embodiments of the method, the first step, the second step and the third step of the device contain a first fluid that is substantially static. Specific embodiments of the method include introducing a second fluid into the inlet portion and through the first step, the second step and the third step. In particular embodiments, a partial droplet of the second fluid forms in the first step, a complete droplet of the second fluid forms in the second step (or during the transition between the plurality of first steps and the second steps), and the complete droplet of the second fluid is directed from the second step to the third step.

In some embodiments, the complete droplet of the second fluid is compressed in the second step such that a height of the complete droplet in the second step is less than a length of the complete droplet in the second step. In specific embodiments, the complete droplet of the second fluid is compressed in the third step such that a height of the complete droplet in the third step is less than a length of the complete droplet in the third step. In certain embodiments in which the complete droplet of the second fluid is compressed in the third step, the droplet diameter (at its shortest dimension or "height")<SH3<2× the droplet diameter (at its longest dimension or "length"). In some embodiments the complete droplet of the second fluid is not compressed in the third step such that a height of the complete droplet in the third step is equal to the length of the complete droplet in the third step. In particular embodiments, the height of the complete droplet in the second step is less than height of the complete droplet in the third step. In particular embodiments, the length of the droplet forming on the first step is greater than T1. In particular embodiments, the length of the droplet on the droplet forming on the second step is greater than T2. In certain embodiments, the second fluid contains an analyte of interest. In specific embodiments, the second fluid contains one or more assay reagents, and in particular embodiments, the assay reagent is a polymerase chain reaction (PCR) primer, a salt, or an enzyme. In certain embodiments, the length of a droplet on step one and step two is more than the respective tread lengths (e.g. T1 and T2) such that a portion of the droplet that is in contact with the step surface will also be in contact with the step edge on that step.

In some embodiments, the first fluid is an oil. In specific embodiments, the first fluid is a hydrophobic liquid and the second fluid is a hydrophilic liquid. In other embodiments, the first fluid is a hydrophilic liquid and the second fluid is a hydrophobic liquid. In particular embodiments, either the first fluid or the second fluid comprises an emulsifying agent, and in certain embodiments, the emulsifying agent comprises a non-ionic surfactant and/or a blocking protein.

In some embodiments of the method, a complete droplet of the second fluid forms in the second step at a rate of at least 10 complete droplets per second. In some embodiments of the method, a complete droplet of the second fluid forms in the second step at a rate of between 1 and 30 complete droplets per second, or more particularly at a rate of between 10 and 30 complete drops per second, or more particularly at a rate of approximately 12, 13, 14, 15, 16, 17, 18, 19, or 20 droplets per second. In some embodiments, a plurality of nozzles are employed to produce at least 100, 200, 300, 400, 500, 600, 700, 800, 900, 1000, 1500, 2000, 3000, 4000, 5000, or any range derivable therein, droplets per emulsion device per second.

In certain embodiments, the complete droplet of second fluid has an average diameter between 40 and 400 microns, 45 and 300 microns, or 40 and 50 microns. Certain embodiments are configured to produce droplets having different diameters, including for example droplets with diameters of 20-60, 80-160, and 200-400 microns. Particular embodiments are configured to produce droplets having different diameters, including for example droplets with diameters of 45, 120, and 300 microns. In specific embodiments, the emulsion formed between the first fluid and the second fluid has a monodispersity (the deviation of the droplet diameter) of less than ten percent. In particular embodiments, the emulsion formed between the first fluid and the second fluid has a monodispersity of one, two, three, four, five, six, seven, or eight percent, or any range derivable therein.

In certain embodiments, the channels and/or steps can be etched in silicon. In particular embodiments, the etched silicon can be covered with glass and/or plastic polymer (plastic, elastomer, rubber, polycarbonate, cyclo-olefin Polymer [COP], etc.), e.g. polydimethylsiloxane (PDMS). In some embodiments, the surfaces of the channel and/or steps may be coated with a hydrophobic composition. In specific embodiments, the hydrophobic composition is perfluorodecyltrichlorosilane (FDTS).

Certain embodiments include a method of forming an emulsion, the method comprising obtaining an emulsification device comprising a first plurality of channels each having an inlet portion, a first step, a second step, and a third step; a second plurality of channels each having an inlet portion, a first step, a second step, and a third step; and a third plurality of channels each having an inlet portion, a first step, a second step, and a third step, wherein the plurality of first steps, the plurality of second steps and the plurality of third steps for the first, second and third pluralities of channels contain a first fluid that is substantially static. Exemplary embodiments of the method may further comprise: introducing a second fluid into the plurality of inlet portions and through the plurality of first steps, the plurality of second steps and the plurality of third steps of the first, second and third pluralities of channels, where: a partial droplet of the second fluid forms in each of the plurality of first steps of the first, second and third pluralities of channels; a first complete droplet of the second fluid forms in a transaction between the plurality of first steps and the plurality of second steps in each of the first plurality of channels; a second complete droplet of the second fluid forms in a transaction between the plurality of first steps and the plurality of second steps in each of the second plurality of channels; and a third complete droplet of the second fluid forms in a transaction between the plurality of first steps and the plurality of second steps in each of the third plurality of channels; the second complete droplet of the second fluid is larger than the first complete droplet of the second fluid; and the third complete droplet of the second fluid is larger than the second complete droplet of the second fluid.

In particular embodiments of the method: the diameter of the first complete droplet is between 25 µm and 65 µm; and the diameter of the second complete droplet is between 80 µm and 200 µm; and the diameter of the third complete droplet is between 200 µm and 400 µm. In specific embodiments of the method: the diameter of the first complete droplet is between 35 µm and 55 µm; the diameter of the second complete droplet is between 100 µm and 140 µm; and the diameter of the third complete droplet is between 250 µm and 350 µm. In certain embodiments of the method, the diameter of the first complete droplet is approximately 45 µm; and the diameter of the second complete droplet is approximately 120 µm; and the diameter of the third complete droplet is approximately 300 µm.

The term "coupled" is defined as connected, although not necessarily directly, and not necessarily mechanically. Two items are "coupleable" if they can be coupled to each other, and, when coupled, may still be characterized as "coupleable." Unless the context explicitly requires otherwise, items that are coupleable are also decoupleable, and vice-versa. One non-limiting way in which a first structure is coupleable to a second structure is for the first structure to be configured to be coupled (or configured to be coupleable) to the second structure.

The terms "a" and "an" are defined as one or more unless this disclosure explicitly requires otherwise.

The term "substantially" and its variations (e.g., "approximately" and "about") are defined as being largely but not necessarily wholly what is specified (and include wholly what is specified) as understood by one of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. For example, a system that comprises four channels may have more than four channels.

A "fluid" generally refers to a substance that tends to flow and to conform to the shape of its container. The fluid may have any suitable viscosity that permits flow. Where two or more fluids are present in a volume, the fluids may be, for example, miscible, slightly miscible, or immiscible. As used herein, two fluids are immiscible, or not miscible, with each other when one is not soluble in the other under the conditions at which the emulsion is used.

As used herein, a "droplet" is an isolated volume of a first fluid that is completely surrounded by a second fluid or is completely surrounded by a second fluid and one or more surfaces. Non-limiting examples of droplets include a hydrophilic liquid suspended in a hydrophobic liquid, a hydrophobic liquid suspended in a hydrophilic liquid, and a gas bubble suspended in a liquid.

An "emulsion" is a suspension of a liquid in a liquid. In some embodiments, the emulsion may be a "microemulsion" or a "nanoemulsion," i.e., an emulsion in which the dispersed phase has an average diameter on the order of micrometers or nanometers, respectively. An emulsion may be created, for example, by allowing droplets of the desired size or sizes to enter into a solution that is immiscible with the droplets. In certain embodiments, a fluidic stream or fluidic droplets may be produced on the microscale in a microchannel (i.e., a channel or step having an average cross-sectional dimension of between about 1 µm to 1 mm).

A fluid that is "substantially static" is a fluid in which flow-induced pressure variations are negligible. For example, in various embodiments disclosed herein a first fluid is substantially static in a channel and a second fluid, which is immiscible with the first fluid, flows into the channel via an inlet. The second fluid may be caused to flow through the inlet by, for example, a pump. The substantially static first fluid may have some movement due to displacement of the first fluid by the second fluid flowing into the channel; but there is no additional inlet conveying a flow of the first fluid into the channel. There may, however, be an outlet or waste channel to accommodate any of the first fluid that is displaced from the channel by the second fluid. In other words, the first fluid is "passive." Also, because the first fluid is passive and does not co-flow with the second fluid, the flow rate does not determine droplet size as it does in other co-flow droplet formation technologies such as T-junction devices.

The inlet portion, first step, and second step may be referred to collectively herein as a "nozzle." An emulsification device may have a single nozzle or a plurality of nozzles. A plurality of nozzles may be in fluid communication with a common third step or a plurality of nozzles may each be in fluid communication with a plurality of separated third steps. A plurality of nozzles will have a plurality of inlet portions, but the first step may be a single continuous step in fluid communication with the plurality of inlet portions or the first step may be a plurality of structurally distinct first steps each in fluid communication with a dedicated inlet portion of the plurality of inlet portions. Likewise, the second step may be a single continuous step in fluid communication with the first step or first steps, or the second step may be a plurality of structurally distinct second steps each in fluid communication with a dedicated first step of a plurality of first steps.

Furthermore, a device or structure that is configured in a certain way is configured in at least that way, but may also be configured in ways that are not listed. Metric units may be derived from the English units provided by applying a conversion and rounding to the nearest micrometer.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention. It is understood that for purposes of clarity, not all reference numbers are shown for every component visible in each figure.

It should be understood that the present devices and methods are not intended to be limited to the particular forms disclosed. Rather, they are to cover all modifications, equivalents, and alternatives falling within the scope of the claims.

Figure 1A:
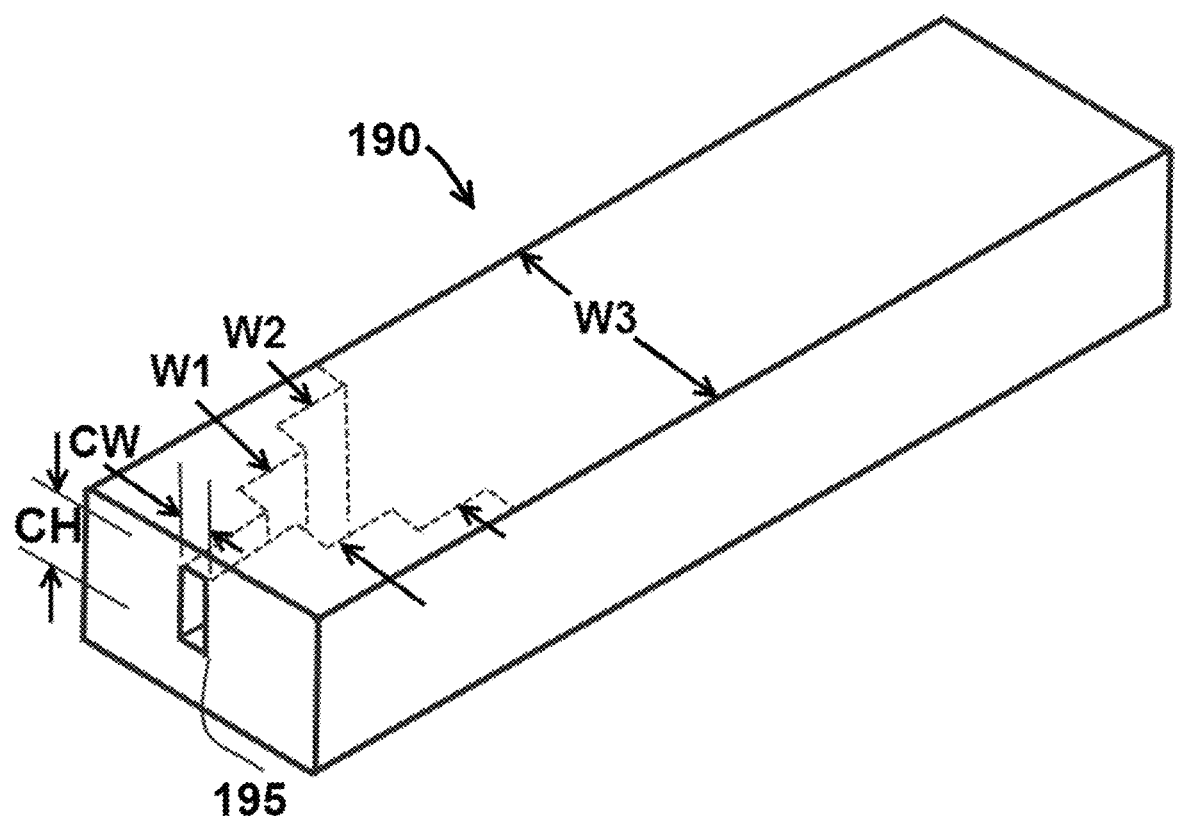
FIG. 1A is a perspective view of an exemplary embodiment of a multi-step emulsification device according to the present disclosure.

FIG. 1A illustrates an emulsification device 190 in perspective view. In this embodiment, emulsification device 190 comprises an inlet channel 195 with a channel width CW and a channel height CH. Inlet channel 195 further comprises portions of increasing width. For example, inlet channel 195 comprises a portion with a width W1 that is greater than width CW. In particular embodiments, the ratio of W1/CW may be greater than 2.0, greater than 5.0, greater than 10.0, greater than 50.0, or greater than 100.0. In specific embodiments the ratio of W1/CW may be between 5.0 and 25.0. In the embodiment shown, inlet channel 195 comprises further portions with increasing widths W2 and W3.

Figure 1B:
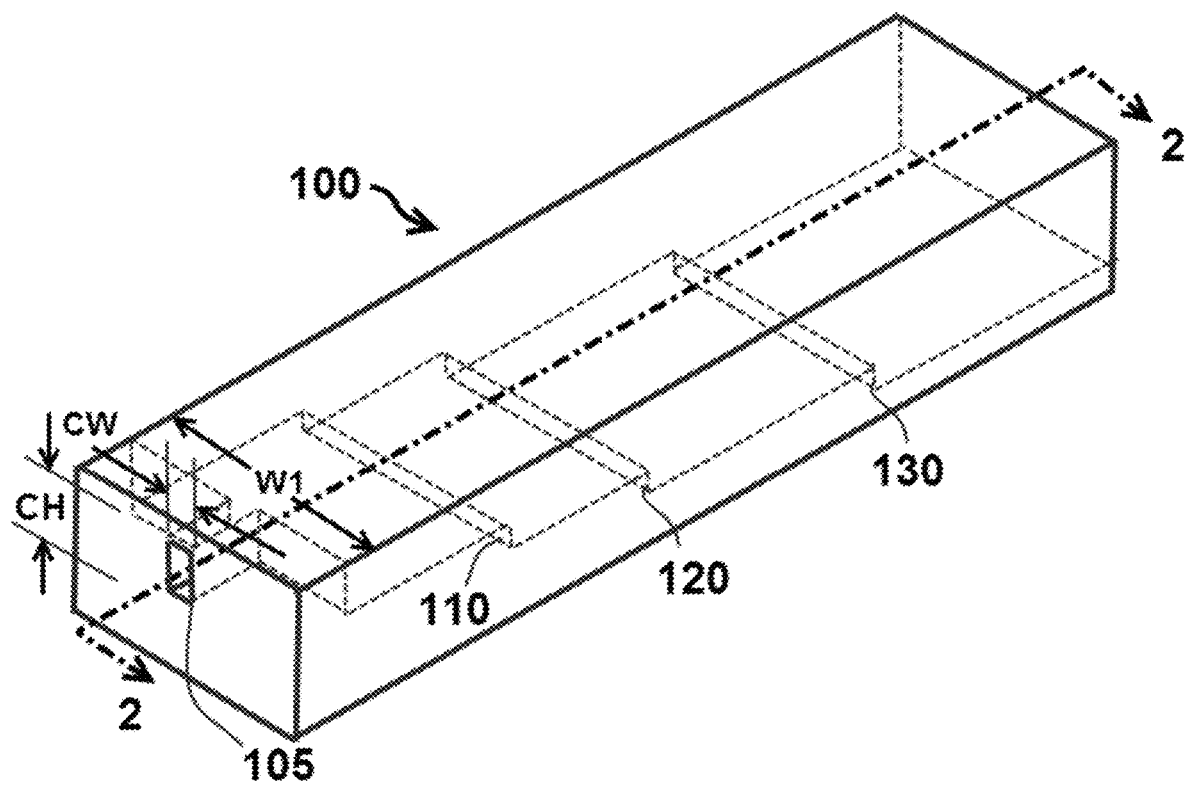
FIG. 1B is a perspective view of an exemplary embodiment of a multi-step emulsification device according to the present disclosure.
Figure 2:
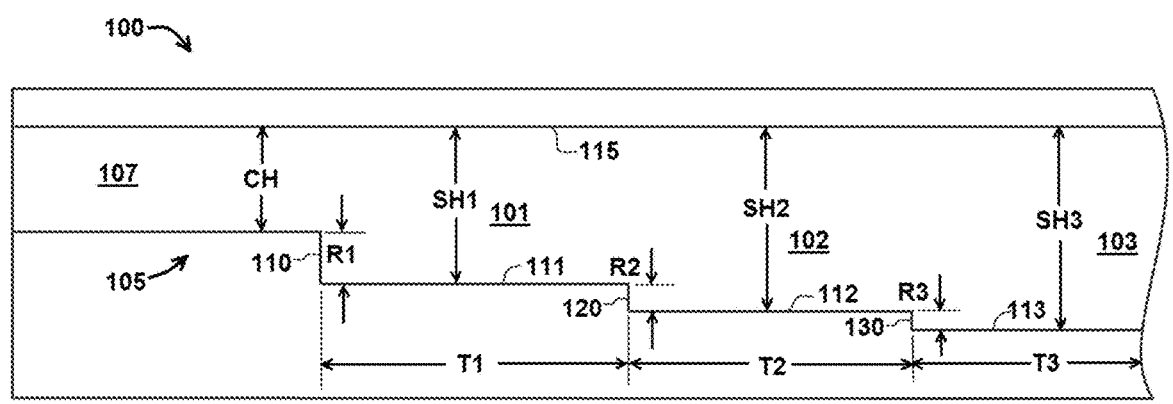
FIG. 2 is a section view of the embodiment of FIG. 1B.
Figure 3A:
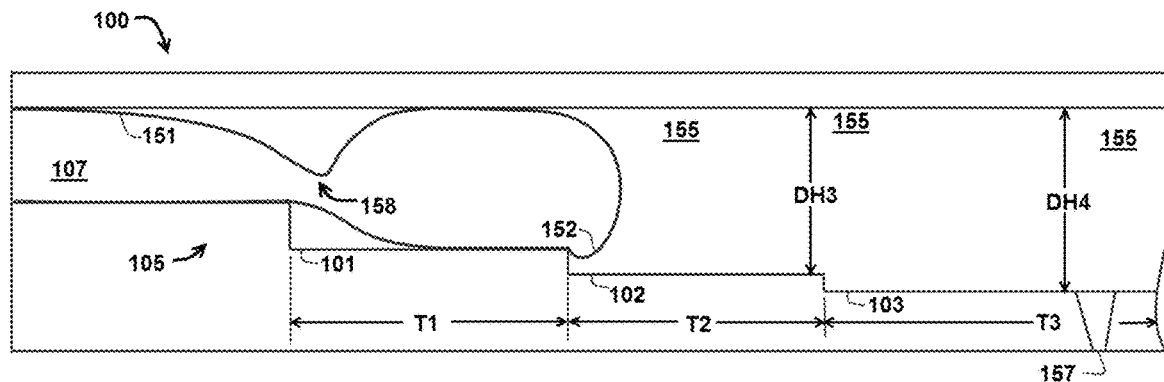
FIGS. 3A-3C are section views of the embodiment of FIG. 1B during operation.
Figure 3B:
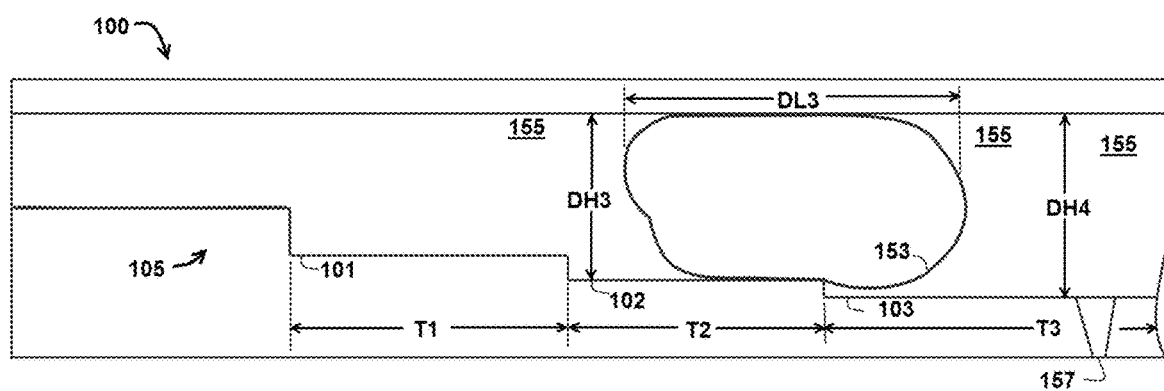
Figure 3C:
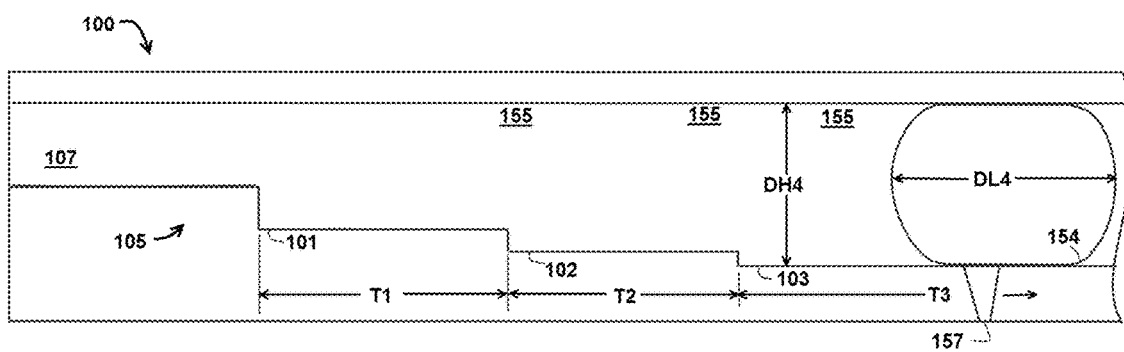

FIGS. 1B and 2 respectively illustrate an emulsification device 100 in perspective and section views. The embodiment in FIG. 1B and FIG. 2 includes a channel 105 with risers 110, 120 and 130 and steps 101, 102 and 103 as described further below. For purposes of clarity, not all elements are labeled in both FIG. 1B and FIG. 2. In the embodiment in FIG. 1B, channel 105 includes an inlet portion having a channel width CW and a channel height CH. Channel 105 further includes a portion having a width W1 that is greater than CH. In some embodiments, a plurality of inlet portions may be in fluid communication with a common first step, in which case the width W1 of this common step would be significantly greater than the width CW of any individual inlet portion. The width W1 of this common step would be greater than the sum of all widths of the inlet portions in fluid communication with the step FIGS. 3A-3C illustrate section views of emulsification device 100 during operation.

In the embodiment shown in FIG. 1B and FIG. 2, emulsification device 100 comprises a multi-step configuration comprising a channel 105 having an inlet portion 107, a first step 101, a second step 102, and a third step 103, each in fluid communication with the other. In addition, emulsification device 100 comprises a first riser 110 at the interface of inlet portion 107 and first step 101, a second riser 120 at the interface of first step 101 and second step 102, and a third riser 130 at the interface of second step 102 and third step 103. First step 101 comprises a first step height SH1 and a first tread length T1, second step 102 comprises a second step height SH2 and a second tread length T2, and third step 103 comprises a third step height SH3 and a third tread length T3.

As used herein, the tread length T1 equals the distance between first riser 110 and second riser 120, tread length T2 equals the distance between second riser 120 and third riser 130, and tread length T3 equals the distance between third riser 130 and the end of a droplet collection chamber of the emulsification device 100 that is distal from inlet portion 107 or tread length T3 equals the distance between third riser 130 and a fourth riser if the emulsion device comprises one or more additional steps. In addition, SH1 equals the distance between opposing surfaces 115 and 111, SH2 equals the distance between opposing surfaces 115 and 112, and SH3 equals the distance between opposing surfaces 115 and 113. In the illustrated embodiment, surface 115 is distal from first, second and third risers 110, 120 and 130. In the embodiment shown, surface 111 extends between first and second risers 110 and 120, and surface 111 is parallel to surface 115. Similarly, surface 112 extends between second and third risers 120 and 130, and surface 112 is parallel to surface 115 in this embodiment. Furthermore, surface 113 is parallel to surface 115 and extends from riser 130 to the end of emulsification device 100 that is distal from inlet portion 107. In the illustrated embodiment, first, second and third risers 110, 120 and 130 are perpendicular to surface 115.

As explained further below, the dimensions and geometry of the channel and steps are configured to produce highly monodispersed emulsions at high frequency from a single fluid flow. As demonstrated by the data presented below, a multi-step configuration can provide significant improvement in monodispersity over a single-step design. Without wishing to be bound by theory, it is believed that the inferior performance of the single-step design can be attributed to the fact that the forming droplets would contact previously formed droplets in unpredictable ways, thus affecting the forming droplet size. The multi-step configuration disclosed herein solves the inferior monodispersity issue of the single-step design. In particular, the multi-step configuration defines multiple sections serving specific functions in droplet formation.

In the illustrated embodiment, inlet portion 107 comprises a channel height CH and a channel width CW (shown in FIG. 1). In particular embodiments, the ratio of CW/CH is greater than 0.2 and less than 5.0. Inlet portion 107 is in fluid communication with first step 101, which comprises a tread length T1 and a step height SH1, where SH1 is greater than channel height CH by a riser height R1 that is greater than zero. In specific embodiments, the ratio of first step height to channel height SH1/CH is greater than 1.0 and less than 5.0. While exemplary embodiments shown and described herein include nozzles arranged in a linear configuration, other embodiments may include different nozzle arrangements, including for example, a circular arrangement of nozzles.

It is understood that dimensional terms, such as height, width, and length are used for reference purposes only and not intended to require a particular orientation of microchannel emulsification device 100. As used in reference to FIGS. 2 and 3A-3C, height refers to a vertical dimension (e.g. top to bottom of the illustration page), width refers to a dimension perpendicular to the plane of the illustrated section view (e.g. perpendicular to the page), and length refers to the a horizontal dimension (e.g. left to right of the page). In general, the terms height and length refer to perpendicular dimensions in one plane, while the term width refers to a dimension perpendicular to the plane of the height and length.

In the embodiment shown, SH1 is greater than CH by riser height R1 (e.g. the dimensional difference between SH1 and CH). In addition, SH2 is greater than SH1 by a riser height R2, and SH3 is greater than SH2 by a riser height R3. The various riser heights R1, R2 and R3 are shown extending downward in the vertical direction in FIG. 2. It is understood, however, that the riser heights may also extend in the upward or side direction. The droplet remains confined (i.e., non-spherical) in the nozzle and, therefore, surface tension, not gravity, is the primary force affecting droplet formation during operation of exemplary embodiments, allowing the riser heights to be formed in any direction (e.g., downward, upward, or side) if desired. Either CH or CW (whichever dimension is smaller) are primary factors in determining the diameter of droplets formed by device 100, and SH1 or W1 are secondary factors in determining the diameter of droplets formed by device 100.

In the illustrated embodiment, inlet portion 107 of channel 105 has a width-to-height ratio (CW/CH) that is greater than 0.2 and less than 5.0. In certain embodiments, the ratio of CW/CH may be greater than 1.5 and less than 4.5, and in particular embodiments, the ratio of CW/CH may be greater than 2.5 and less than 3.5, and in specific embodiments the ratio of CW/CH may be approximately 3.0.

As previously mentioned, first step 101 is in fluid communication with inlet portion 107, and height SH1 of first step 101 is greater than CH by a riser height R1. In exemplary embodiments, the ratio of SH1/CH is greater than 1.0 and less than 5.0, or greater than 1.25 and less than 2.75 or greater than 1.5 and less than 2.5, or greater than 1.75 and less than 2.25, or greater than 1.25 and less than 1.75.

Emulsification device 100 also comprises a second step 102 in fluid communication with first step 101, and height SH2 of second step 102 is greater than SH1 by a riser height R2. In exemplary embodiments, the ratio of SH2/CH is greater than 0.1 and less than 5.0. In addition, emulsification device 100 also comprises a third step 103 in fluid communication with second step 102, and step height SH3 of third step 103 is greater than SH2 by a riser height R3. In exemplary embodiments, R3 is greater than 0.1 micron and less than 1000 microns. In the embodiment shown, R1 is greater than R2, and R2 is greater than R3. However, in other embodiments R3 is greater than R2, and R2 is greater in R1. In some embodiments, R3 is greater than R2, and R2 is equal to R1. Furthermore, the embodiment shown includes a ratio of T1/CH between 0.1 and 7.0 and a ratio of T2/CH that is less than T1/CH.

In particular embodiments, the ratio of T1/R1 is greater than 2.0, or greater than 5.0 or greater than 10.0. In certain embodiments the ratio of T2/R2 is greater than 2.0, or greater than 5.0 or greater than 10.0.

FIGS. 3A-3C illustrate emulsification device 100 during operation. For purposes of clarity, not all elements of emulsification device 100 are labeled in FIGS. 3A-3C. Reference can be made to FIG. 2 for elements not labeled in FIGS. 3A-3C. FIG. 3A illustrates a partial droplet 152 transitioning from first step 101 to second step 102. FIG. 3B illustrates a droplet 153 transitioning from second step 102 to third step 103. FIG. 3C illustrates a droplet 154 on third step 103. Referring initially to FIG. 3A, during operation a fluid stream 151 can be introduced (e.g., directed in a flowing stream from a higher pressure to a lower pressure) into inlet portion 107. Inlet portion 107 is configured to deliver a sample thread 151 to first riser 110 with height R1 between inlet portion 107 and first step 101.

In particular embodiments, fluid stream 151 may be a sample thread comprising a hydrophilic liquid, while steps 101, 102 and 103 contain a fluid 155 that is a hydrophobic liquid. In some embodiments, fluid stream 151 may comprise a hydrophobic liquid, while fluid 155 comprises a hydrophilic liquid. In certain embodiments, steps 101, 102 and 103 are filled with fluid 155 comprising a hydrophobic liquid (e.g. an oil) prior to the introduction of fluid stream 151 comprising a hydrophilic liquid (e.g. an aqueous fluid) into first channel 101. In exemplary embodiments, fluid 155 is substantially static when fluid stream 151 is introduced into inlet portion 107 of first channel 105. Further examples of the types of liquids that may be used for droplet formation in emulsification device 100 are provided below in the section entitled "EMULSIONS".

First step 101 is configured to begin destabilization of a fluid steam 151 (e.g., transitioning a contiguous fluid stream 151 to contain a discontinuity), and partial droplet 152 is formed in first step 101. In certain embodiments, partial droplet 152 is approximately ninety percent formed (as measured by volume) in first step 101 during operation. In exemplary embodiments, first step 101 does not provide for complete droplet formation, and partial droplet 152 is fluidically connected to fluid stream 151. As shown in FIG. 3A, partial droplet 152 is fluidically connected to fluid stream 151 by a region 158 that has a smaller cross-sectional area than fluid stream 151 or partial droplet 152 (e.g., fluid stream 151 necks down into region 158 before forming partial droplet 152). Partial droplet 152 is compressed by first step 101 and extends the entire height SH1 of first step 101. According to fluid dynamics and physics principles, partial droplet 152 will seek the lowest possible energy state (e.g. an uncompressed state). Accordingly, partial droplet 152 will continue to progress toward second step 102 until it is contact with first riser 110, where the droplet will be less compressed than it is in first step 101 due to second step 102 having a height SH2 that is greater than first step 101 height SH1.

In exemplary embodiments, partial droplet 152 will form a complete droplet 153 (as shown in FIG. 3B) upon reaching second riser 120 at the interface of first step 101 and second step 102. During operation, fluid stream 151 will be introduced into first channel 101 over a period of time. When one partial droplet 152 progresses to form a complete droplet 153, a subsequent partial droplet will form in first step 101. Second step 102 and riser 120 (with riser height R2) are configured to form a complete droplet 153 that is separated from a partial droplet 152 (and fluid stream 151).

Second step 102 is also configured to provide a protection zone between first step 101 where partial droplets 152 are forming and third step 103 where complete droplets 154 are stored. As such, contact between formed, complete droplets and forming, partial droplets is reduced or eliminated. The lengths of steps 101 and 102 (e.g. dimensions T1 and T2) are sized to accommodate the droplet in those respective sections so that each section can properly accomplish its function. Theoretical calculations for desired droplet formation and advancement indicate a tread length T1=3.807 (CH) and a tread length T2=1.8585 (CH). Actual tread lengths may vary from the dimension theoretically calculated. This is in contrast to a continuous ramp configuration or a configuration with a series of steps arranged to approximate a ramp where the function of each step is identical. Moreover, the multi-step channel disclosed herein also provides manufacturing options that are not available for a continuous ramp configuration by allowing for increased tolerances.

In exemplary embodiments, complete droplet 153 is compressed within step 102 such that it is not completely spherical in shape. For example, complete droplet 153 has a height DH3 equivalent to SH2 (the height of step 102, shown in FIG. 2). In addition, droplet 153 also has a length DL3 that is greater than DH3. According to fluid dynamics and physics principles, droplet 153 will seek the lowest possible energy state (e.g. an uncompressed state). Accordingly, droplet 153 will continue to progress toward third step 103 until it reaches second riser 120, where the droplet will be less compressed than it is in second step 102 due to third step 103 having a height SH3 that is greater than second step 102 height SH2.

In the embodiment shown, third step 103 is configured to provide storage and, optionally, imaging of droplet 154 via an imaging device 157 (e.g. a camera or photosensitive detector). Additional information regarding optional imaging of droplet 154 is provided below in the section entitled "DROPLET IMAGING." Droplet 154 is also a complete droplet that may or may not be completely spherical, but is less compressed than droplet 153. Accordingly, droplet 154 height DH4 is greater than droplet 153 height DH3, but usually less than droplet 154 length DL4. It is understood that FIG. 3C is a section view and multiple droplets 154 can be located in third step 103 during operation.

Figure 4:
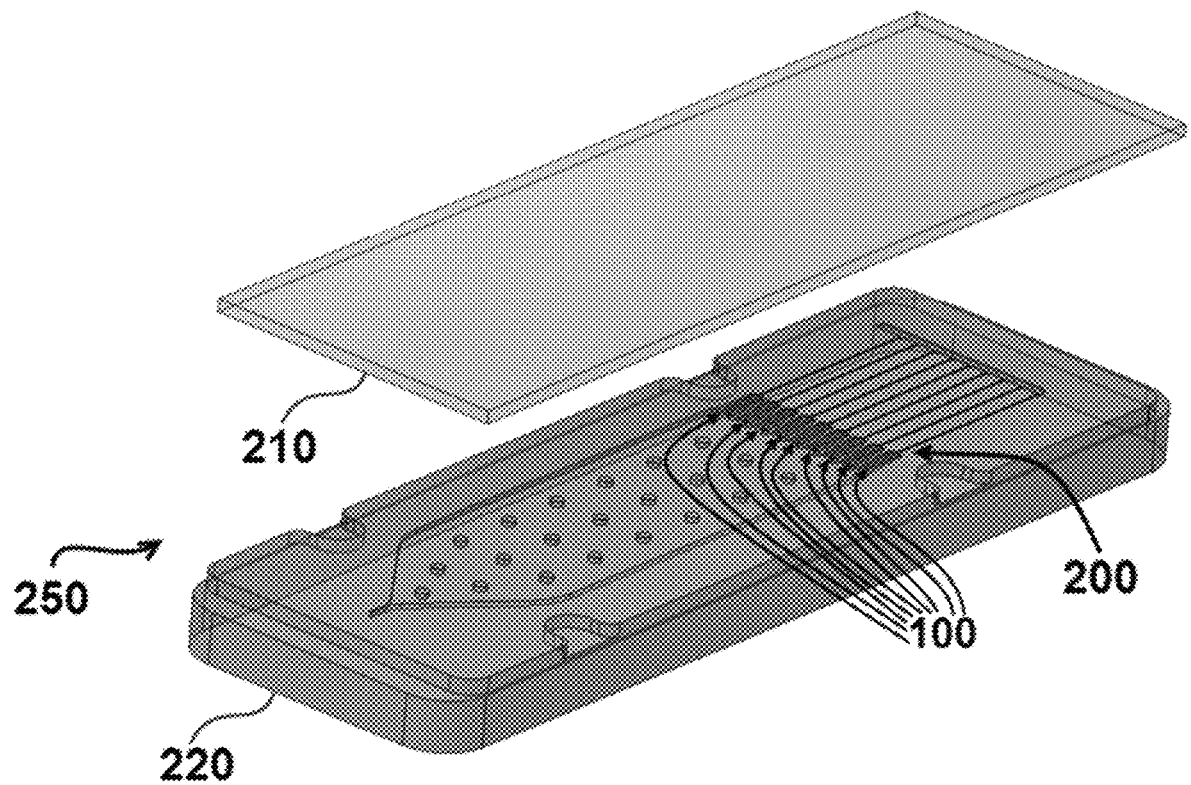
FIG. 4 is a perspective view of a device comprising a plurality of nozzles according to the present disclosure.

FIG. 4 illustrates an exploded assembly perspective view of an emulsification device 250 that comprises a plurality of nozzles 200. In exemplary embodiments, each nozzle 200 may comprise a channel and steps with features equivalent to those described herein for the channel and steps of emulsification device 100. In the embodiment shown, emulsification device 250 comprises nine parallel nozzles 200. Other embodiments may comprise a greater or fewer number of nozzles. In the embodiment shown, emulsification device 250 comprises a base 220 comprised of polydimethylsiloxane (PDMS) and a cover 210 comprised of glass.

Figure 5:
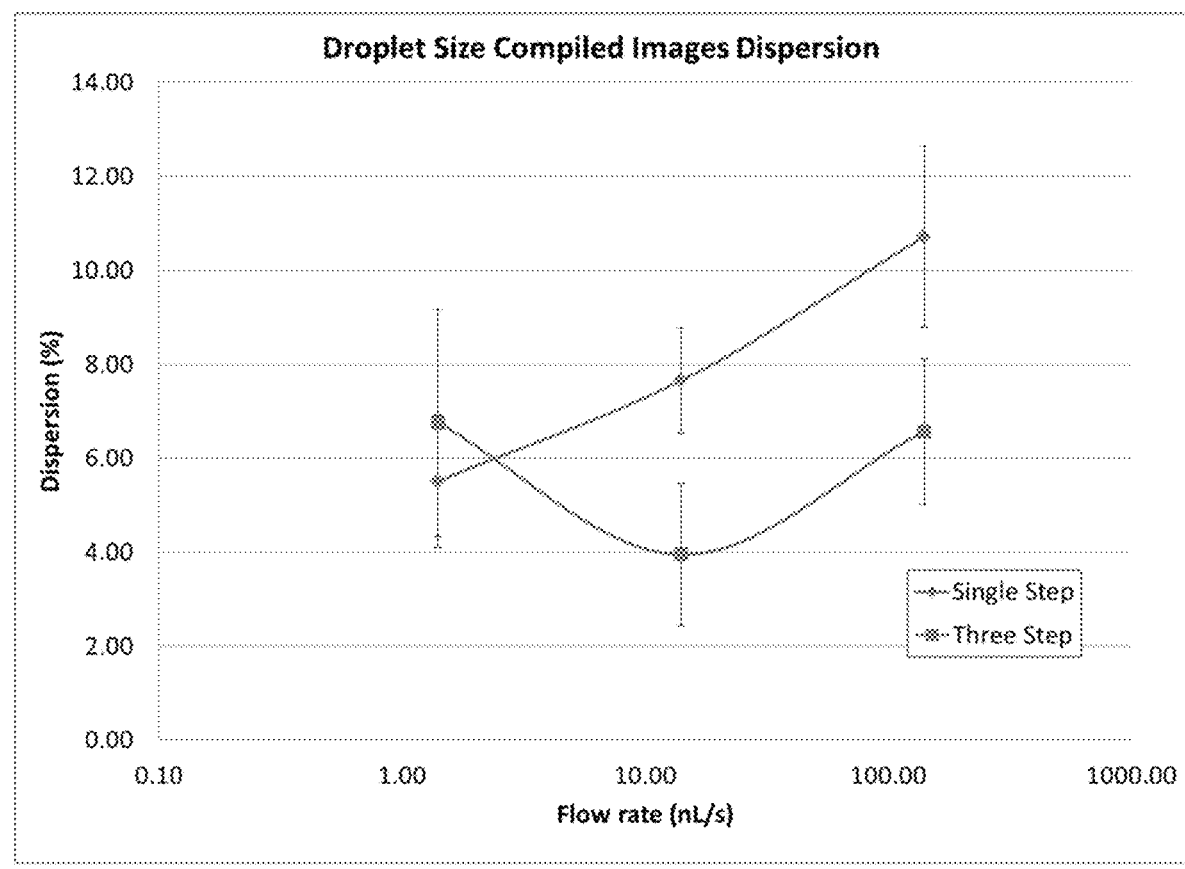
FIG. 5 is a graph illustrating dispersion percentage versus flow rate for a network of single-step emulsification devices and a network of multi-step emulsification devices.

FIG. 5 graphically illustrates dispersion percentage versus flow rate for a network of sixteen single-step emulsification devices and a network of sixteen multi-step nozzles. The single-step emulsification devices comprised a step height of approximately 189 µm. CellProfiler software and an imaging processing pipeline were used to detect fluorescently labeled droplets. Multiple images were acquired during each test, with approximately 300 droplets each. The software created files with a list of all droplets found along with associated droplet diameters for all files, and the average and standard deviation of the diameters were then calculated. The dispersion was calculated and compared between the two configurations, where the dispersion is the coefficient of variation (CV) of the diameter, and where the CV is equal to the standard deviation divided by the mean diameter. The channel dimensions used during this test included a channel height of 20 µm, a channel width of 60 µm, and a ratio of CH/SH1=0.666 or R1/CH=0.5.

Figure 6:
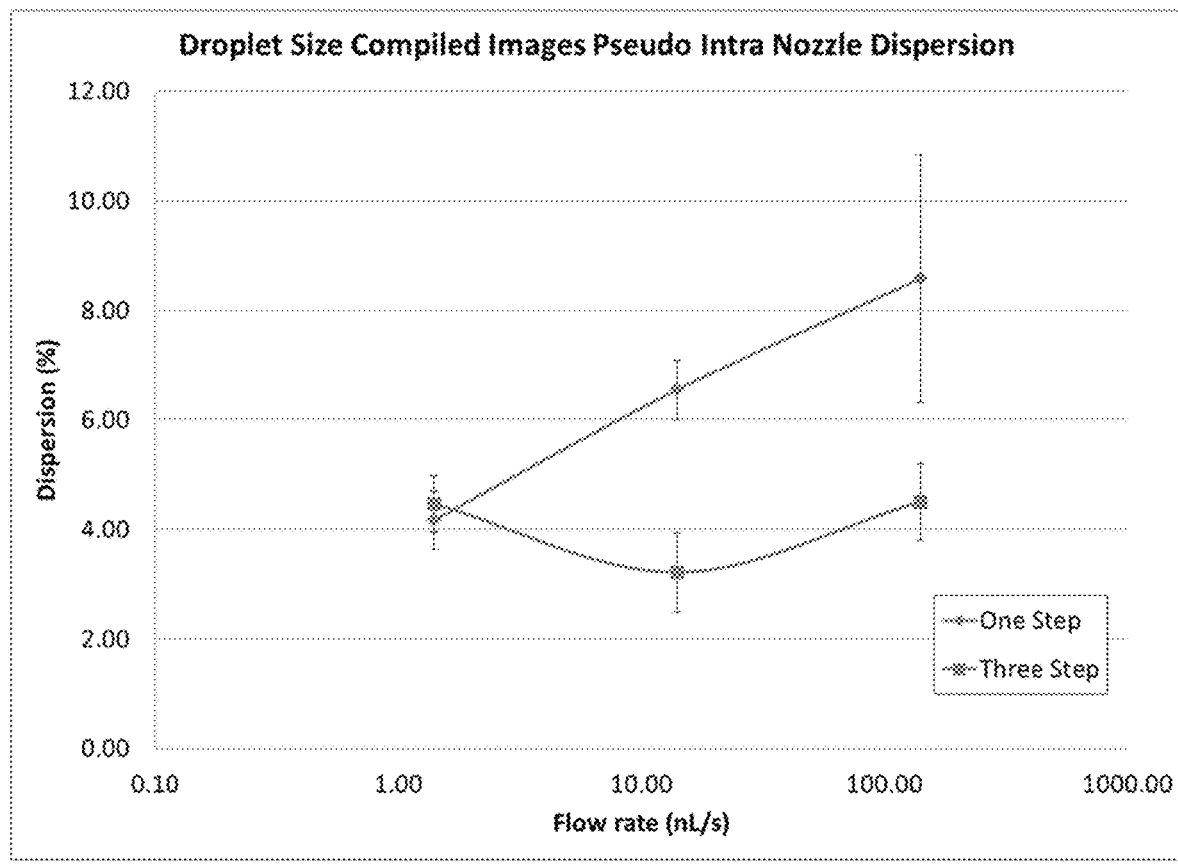
FIG. 6 is a graph illustrating dispersion percentage versus flow rate as calculated for a single-step emulsification device and a multi-step emulsification device of the networks of devices from FIG. 5.

FIG. 6 is a graph illustrating dispersion percentage versus flow rate as calculated for a single-step emulsification device and a multi-step emulsification device as shown in FIG. 4.

Figure 7:
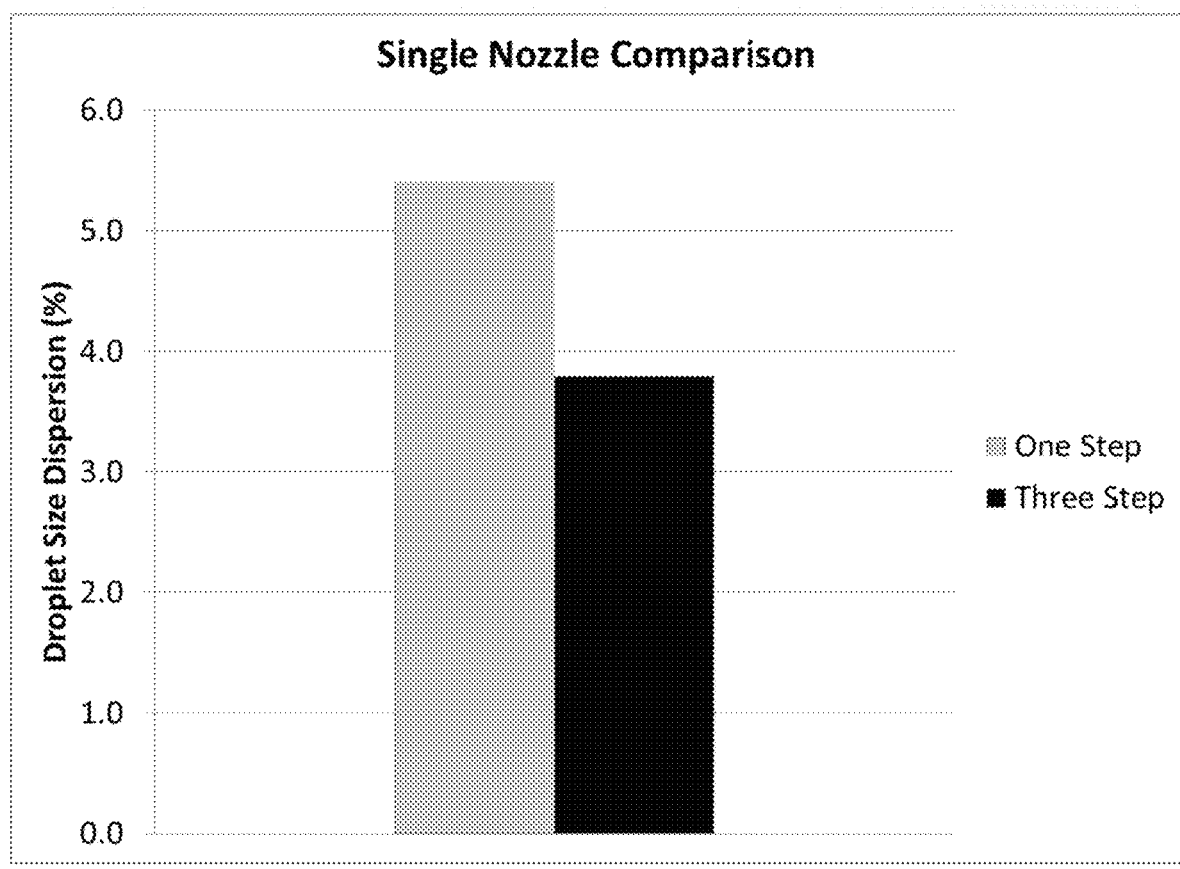
FIG. 7 is a chart illustrating droplet size dispersion percentage for a single-step emulsification device and a multi-step emulsification device

FIG. 7 is a chart illustrating droplet size dispersion percentage for a single-step emulsification device and a multi-step emulsification device. The channel dimensions used during this test included a channel height of 25 µm, a channel width of 60 µm, and a delta height/height equal to 0.5.

In certain embodiments, an emulsification device can be configured to generate multiple droplet sizes. For example, an emulsification device may comprise multiple sets of nozzles and channels with different geometries to generate droplets with different sizes and volumes.

Figure 8:
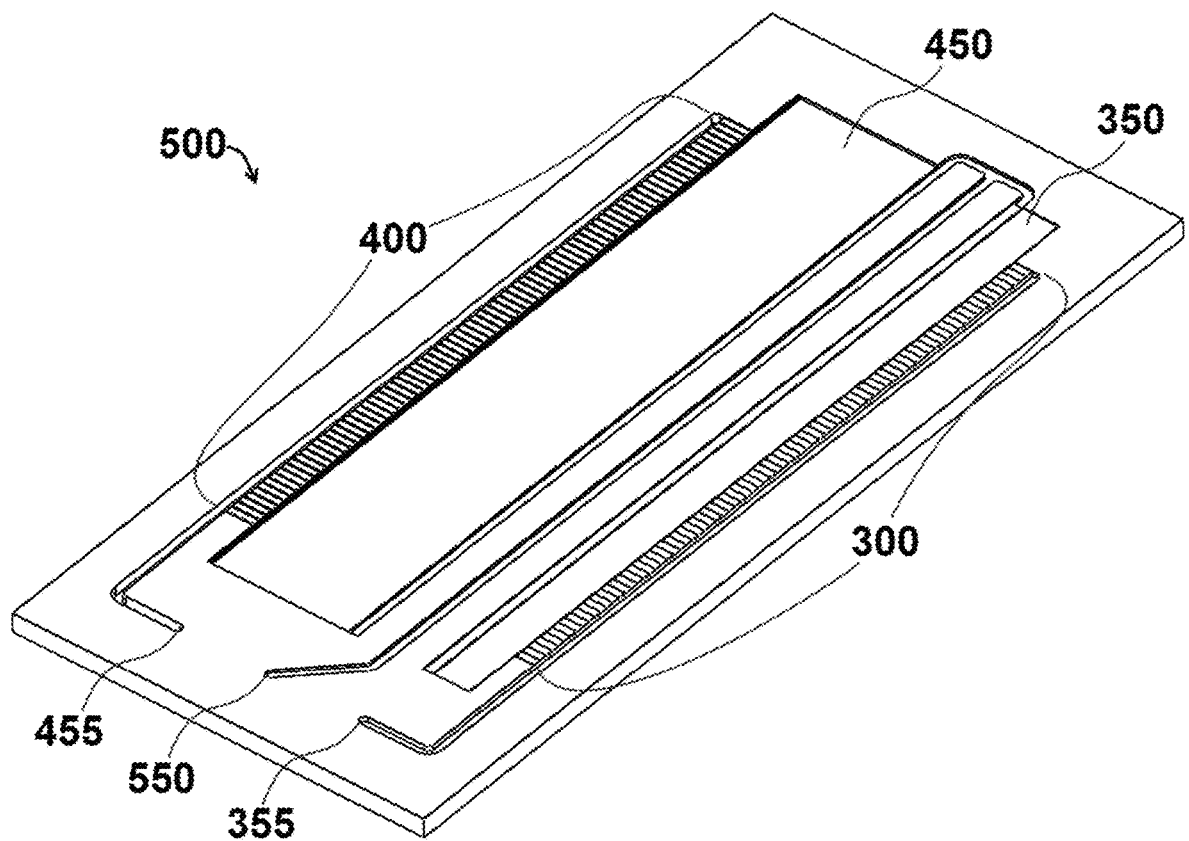
FIG. 8 is a perspective view of an exemplary embodiment of a multi-step emulsification device according to the present disclosure.
Figure 9:
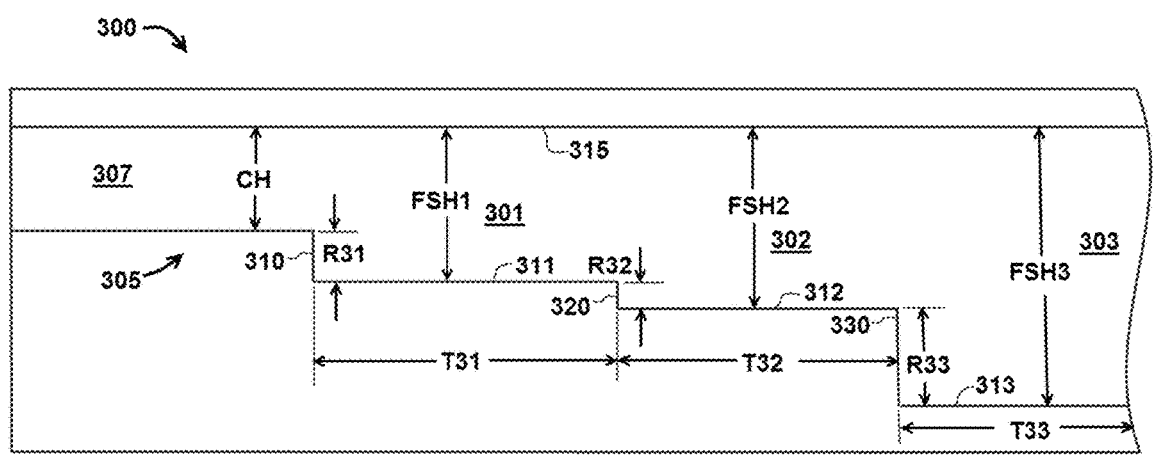
FIG. 9 is a partial section view of the embodiment of FIG. 8.
Figure 10:
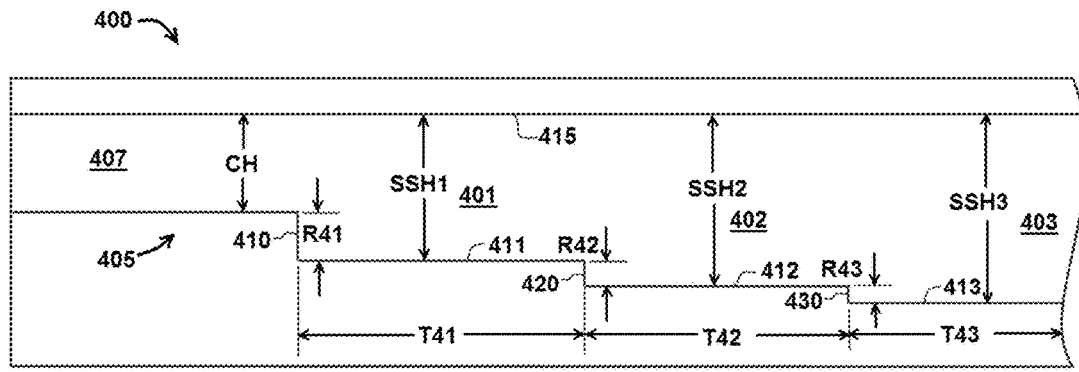
FIG. 10 is a partial section view of the embodiment of FIG. 8.

Referring now to FIG. 8, an emulsification device 500 comprises a first plurality of nozzles 300 and a second plurality of nozzles 400. In the embodiment shown, nozzles 300 are supplied fluid with a fluid supply channel 355, while nozzles 400 are supplied fluid with a fluid supply channel 455. Droplets formed by nozzles 300 and 400 are collected in collection chambers 350 and 450, respectively. Device 500 further comprises a waste channel 550 configured to allow waste material (e.g. excess fluid or droplets) to exit emulsification device 500 and be directed to a waste collection chamber. In exemplary embodiments, each nozzle 300 and 400 may comprise a channel and steps with features equivalent to those of other embodiments described herein. For example, each nozzle in first and second plurality of nozzles 300 and 400 may comprise a channel 305 and 405, as shown in FIGS. 9 and 10, respectively. Channels 305 and 405 can be configured with features equivalent to those described herein for the channels and steps of emulsification device 100.

During operation, nozzles 300 and 400 can be configured to generate droplets having different diameters. For example, each channel 405 can be configured to generate droplets with a diameter that is greater than the diameter of droplets generated from each channel 305. In addition, emulsification device 500 can be configured to control the number of droplets generated by each plurality of channels 305 and 405. For example, fluid supply channels 355 and 455 can be configured such to control the amount of fluid supplied to channels 305 and 405. In certain embodiments, fluid supply channels 355 and 455 may have different diameters, lengths, and/or other factors that can affect the resistance of fluid flow through the channels and bias the amount of fluid flow to channels 305 and 405. In other embodiments, fluid supply channels 355 and 455 may comprise valves that can be manipulated to control the amount of fluid flow to channels 305 and 405. Such configurations can provide differing amounts of fluid flow to channels 305 and 405, allowing for different numbers of droplets to be formed by channels 305 and 405. The ability to individually control the fluid flow to channels 305 and 405 can be used to precisely control the percentage of smaller diameter droplets formed by channels 405 and the percentage of larger diameter droplets formed by channels 305. The ability to generate droplets of different sizes can provide significant advantages over other emulsification devices that generate droplets of generally equivalent sizes. For example, the different size droplets generated by emulsification device 500 can be used to increase the dynamic range available during a digital PCR analysis.

In particular embodiments, channels 305 and 405 may have geometries similar to those of previously described embodiments. For example as shown in the cross-section view of FIG. 9, channel 305 has an inlet portion 307, a first step 301, a second step 302, and a third step 303, each in fluid communication with the other. In addition, channel 305 comprises a first riser 310 (with riser height R31) at the interface of inlet portion 307 and first step 301, a second riser 320 (with riser height R32) at the interface of first step 301 and second step 302, and a third riser 330 (with riser height R33) at the interface of second step 302 and third step 303. First step 301 comprises a first step height FSH1 and a first tread length T31, second step 302 comprises a second step height FSH2 and a second tread length T32, and third step 303 comprises a third step height FSH3 and a third tread length T33.

In the embodiment shown in FIG. 9, FSH1 equals the distance between opposing surfaces 315 and 311, FSH2 equals the distance between opposing surfaces 315 and 312, and FSH3 equals the distance between opposing surfaces 315 and 313. In the illustrated embodiment, surface 315 is distal from first, second and third risers 310, 320 and 330. In the embodiment shown, surface 311 extends between first and second risers 310 and 320, and surface 311 is parallel to surface 315. Similarly, surface 312 extends between second and third risers 320 and 330, and surface 312 is parallel to surface 315 in this embodiment. Furthermore, surface 313 is parallel to surface 315 and extends from riser 330 to the end of emulsification device 300 that is distal from inlet portion 307. In the illustrated embodiment, first, second and third risers 310, 320 and 330 are perpendicular to surface 315.

Referring now to the cross-section view of FIG. 10, channel 405 has an inlet portion 407, a first step 401, a second step 402, and a third step 403, each in fluid communication with the other. In addition, channel 405 comprises a first riser 410 (with riser height R41) at the interface of inlet portion 407 and first step 401, a second riser 420 (with riser height R42) at the interface of first step 401 and second step 402, and a third riser 430 (with riser height R43) at the interface of second step 402 and third step 403. First step 401 comprises a first step height SSH1 and a first tread length T41, second step 402 comprises a second step height SSH2 and a second tread length T42, and third step 403 comprises a third step height SSH3 and a third tread length T43.

In the embodiment shown in FIG. 10, SSH1 equals the distance between opposing surfaces 415 and 411, SSH2 equals the distance between opposing surfaces 415 and 412, and SSH3 equals the distance between opposing surfaces 415 and 413. In the illustrated embodiment, surface 415 is distal from first, second and third risers 410, 420 and 430. In the embodiment shown, surface 411 extends between first and second risers 410 and 420, and surface 411 is parallel to surface 415. Similarly, surface 412 extends between second and third risers 420 and 430, and surface 412 is parallel to surface 415 in this embodiment. Furthermore, surface 413 is parallel to surface 415 and extends from riser 430 to the end of emulsification device 400 that is distal from inlet portion 407. In the illustrated embodiment, first, second and third risers 410, 420 and 430 are perpendicular to surface 315.

In exemplary embodiments, SSH1 (the first step of the "second" channel [e.g. channel 405]) is larger than FSH1 (the first step height of the "first" channel [e.g. channel 305]). In addition, SSH2 (the "second" channel's second step height) is larger than FSH2 (the "first" channel's second step height). Accordingly, the geometry of channels 405 is configured to form droplets having a diameter that is larger than the diameter of droplets formed by channels 305. In particular embodiments, SSH1 is at least fifty percent greater than FSH1, and in certain embodiments SSH1 is at least one hundred percent greater than FSH1. In addition, SSH2 may be at least fifty percent greater than FSH2 in some embodiments. Such geometries can allow channels 405 to produce droplets having a diameter that is at least fifty percent greater than the diameter of droplets produced by channels 305. In certain embodiments, SSH2 may be at least one hundred percent greater than FSH2, allowing channels 405 to produce droplets having a diameter that is at least one hundred percent greater than the diameter of droplets produced by channels 305. In particular embodiments, SSH3 may be equal to FSH3 as the droplets formed by channels 405 and 305 are directed to a common area in emulsification device 500 (it is understood the drawings in the figures are not to scale unless otherwise noted).

In particular embodiments such as those described in FIG. 9, the diameter of droplets formed by channels 305 may be primarily determined by the dimension of CH or CW of inlet portion 307, whichever is smaller, and secondarily determined by FSH1 as previously described in the discussion of FIGS. 1-3.

Figure 11:
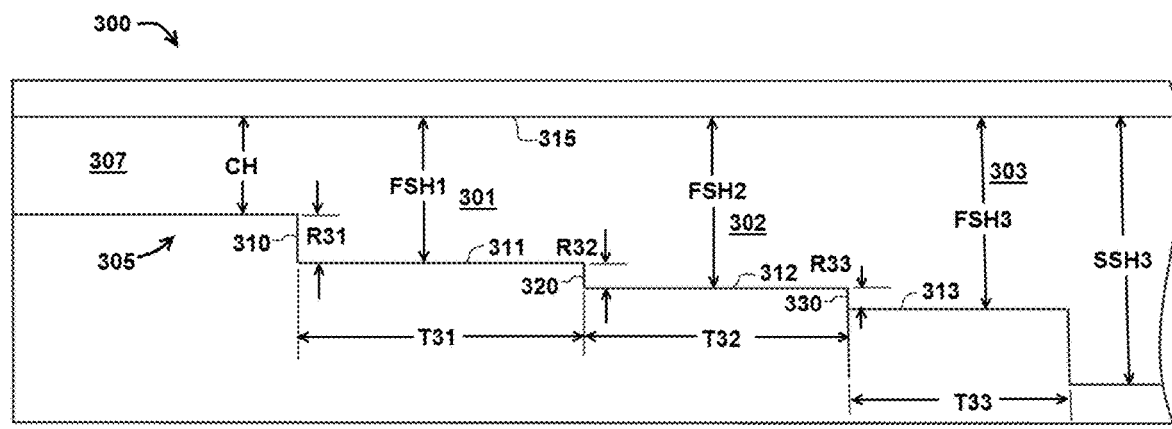
FIG. 11 is a partial section view of the embodiment of FIG. 8.

Referring now to FIG. 11, an alternative embodiment for channels 305 is shown. This embodiment is equivalent to the embodiment shown and described in FIG. 9, with the exception that the value of FSH3 is not equivalent to that of SSH3 and therefore comprises an additional step to provide for advancement of the droplets.

The volume of each droplet formed by channels 305 and 405 is proportional to the cube of the diameter of the droplet (assuming a spherical droplet). In the embodiments shown in FIGS. 9 and 10, if the smaller of dimensions CH and CW for inlet portion 407 is at least fifty percent greater than the smaller of dimensions CH and CW for inlet portion 307, then the diameter of a droplet formed by channel 405 is at least fifty percent greater than the diameter of a droplet formed by 305. As a result, the volume of a droplet formed by a channel 405 is at least 3.375 times greater than the volume of a droplet formed by a channel 305. Similarly, if the smaller of dimensions CH and CW for inlet portion 407 is at least one-hundred percent greater than the smaller of dimensions CH and CW for inlet portion 307, then the diameter of a droplet formed by channel 405 is at least twice the diameter of a droplet formed by 305. Consequently, the volume of a droplet formed by a channel 405 is at least eight times greater than the volume of a droplet formed by a channel 305. It is understood that the dimensional ratios described herein are merely exemplary, and that other embodiments may comprise channel dimensions with values other than those provided in this disclosure.

Figure 12:
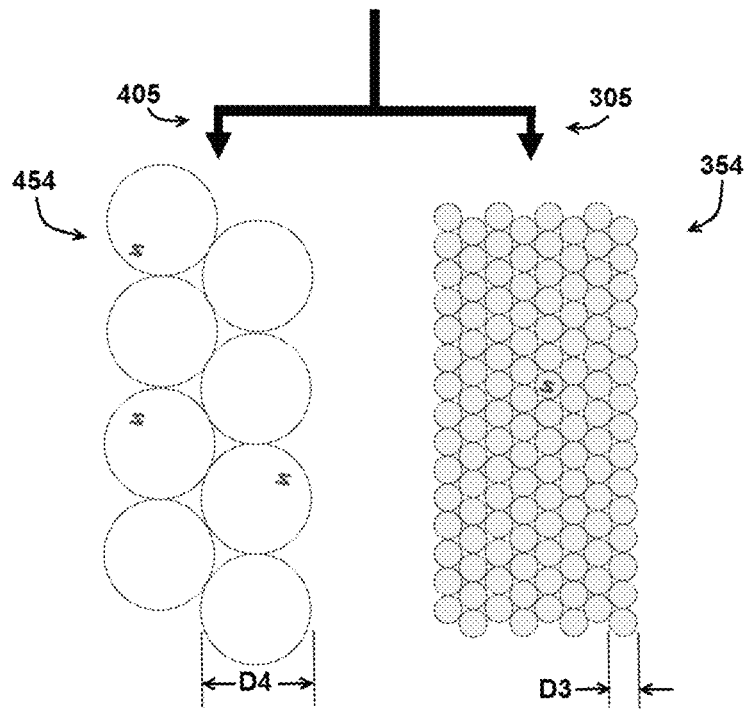
FIG. 12 is a schematic of droplets formed by the exemplary embodiment of FIG. 8.

Referring now to FIG. 12, a schematic of droplets formed by channels 405 and 305 is shown to include different size droplets. In this embodiment, a plurality of droplets 454 are formed by channels 405, while a plurality of droplets 354 are formed by channels 305. As shown, each droplet in the plurality of droplets 454 comprises a diameter D4 that is larger than the diameter D3 of each of the droplets 354. In this embodiment, D3 is determined by dimension CH or CW of inlet portion 307. Similarly, D4 is determined by dimension CH or CW of inlet portion 407.

The ability to generate droplets of varying volumes such as those shown in FIG. 12 can provide numerous benefits during digital PCR analysis. For example, the use of multiple volume droplets provides for a greater dynamic range for a given amount of space and overall volume.

In systems using droplets of uniform volume, the upper limit of the detection is primarily controlled by the volume of each droplet. The lower limit of the detection is generally controlled by the total volume, and therefore number of droplets produced in uniform droplet systems. Therefore, a large dynamic range in a uniform droplet system requires a very large number of small volume droplets. By producing droplets of varying volumes, the dynamic range can be increased for a given volume and area provided as compared to uniform droplet systems. The upper limit of detection can be raised by using droplets with decreased volume. In addition, the lower limit of detection can be reduced by using droplets with increased volume, which allows for the processing of greater sample volumes in the same area.

Figure 13:
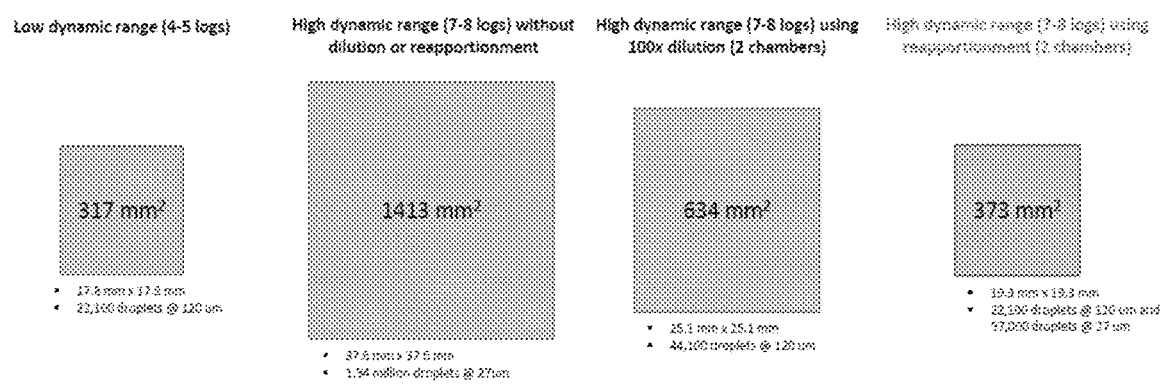
FIG. 13 is a schematic showing different dynamic ranges for varying droplet sizes and areas.

FIG. 13 provides a graphic illustration of the different dynamic ranges for different areas. As shown in the figure, a low dynamic range (e.g. 4-5 logs) of droplets with a 120 µm diameter requires 317 square millimeters. A high dynamic range (e.g. 7-8 logs) without dilution or reapportionment with droplets of 27 µm diameter requires 1,413 square millimeters. A similarly high dynamic range with 100× dilution in two chambers with droplets of 120 µm diameter requires 634 square millimeters. In contrast, a 7-8 logs high dynamic range using two chamber reapportionment with droplets of both 27 µm diameter and 120 µm diameter only requires 373 square millimeters of space. Accordingly, the use of droplets with different diameters can provide for higher dynamic ranges and/or less space required as compared to systems utilizing droplets of uniform size and volume.

Figure 14:
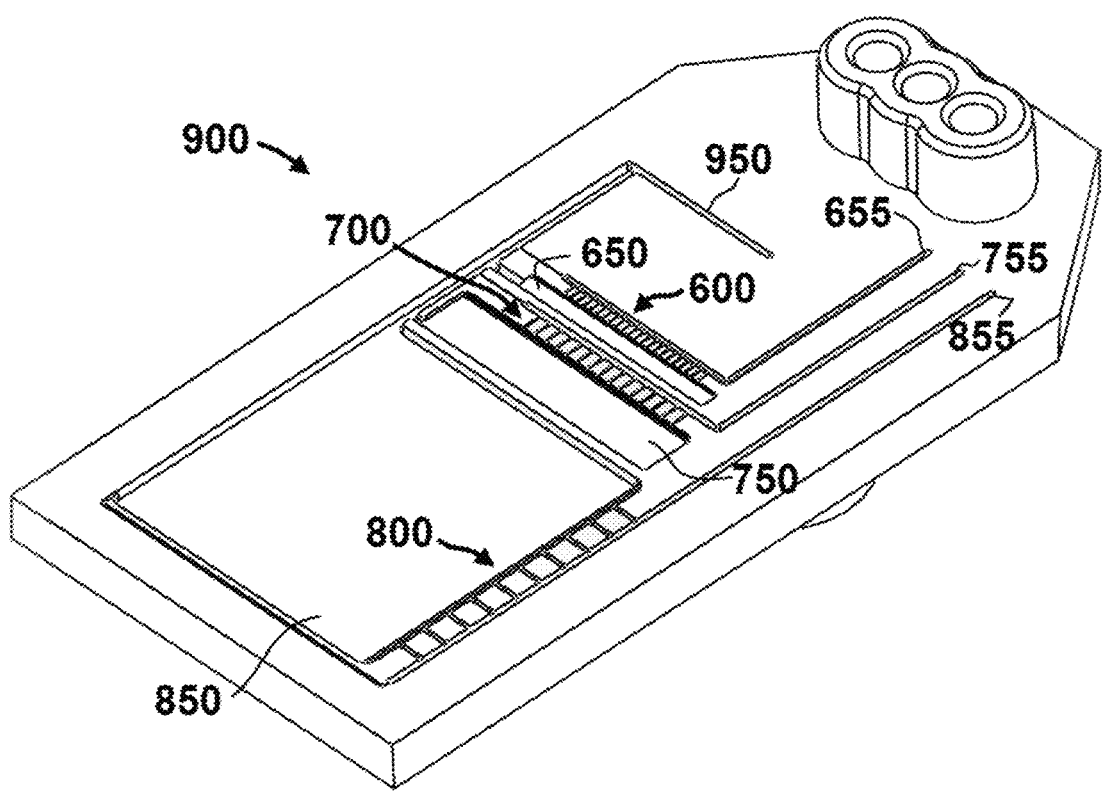
FIG. 14 is a perspective view of an exemplary embodiment of a multi-step emulsification device according to the present disclosure.

While previously-described embodiments are configured to produce droplets of one or two different diameters, other embodiments may be configured to produce droplets of three or more different diameters. Referring now to FIG. 14, an emulsification device 900 comprises a plurality of channels 600, 700, and 800 with fluid supply channels 655, 755 and 855, respectively. In addition, device 900 comprises collection chambers 650, 750 and 850 for channels 600, 700, and 800, respectively. In exemplary embodiments, collection chambers 650, 750 and 850 may have different heights to accommodate droplets of different diameters. Device 900 further comprises a waste channel 950 configured to allow waste material (e.g. excess fluid or droplets) to exit emulsification device 900 and be directed to a waste collection chamber.

Emulsions

Various embodiments disclosed herein employ a water-in-oil emulsion comprising a plurality of aqueous droplets in a non-aqueous continuous phase. All or a subset of the aqueous droplets may contain an analyte of interest. Emulsions are formed by combining two immiscible phases (e.g., water and oil), often in the presence of one or more surfactants. Basic types of emulsions are oil-in-water (o/w), water-in-oil (w/o), and bi-continuous. In droplet-based biological assays, the emulsion will typically be a water-in-oil emulsion with the assay reagents (e.g., PCR primers, salts, enzymes, etc.) contained in the aqueous phase. The "oil" phase may be a single oil or a mixture of different oils. Any suitable non-aqueous fluid may form the non-aqueous continuous phase of the emulsions disclosed herein. In some embodiments, the non-aqueous continuous phase comprises a mineral oil, a silicone oil, or a fluorinated oil (e.g., Fluorinert® FC-40 [Sigma-Aldrich]).

The emulsion may be stabilized by the inclusion of one or more emulsifying agents, which act at the water/oil interface to prevent or delay separation of the phases. Emulsifying agents may also be used to inhibit the merging of adjacent droplets on an array. The compositions disclosed herein may also contain one or more emulsifying agent. In particular embodiments, the emulsifying agent comprises a non-ionic surfactant or a blocking protein. Non-limiting examples of non-ionic surfactants include Tween 20 (polysorbate 20), Triton™ X-100 (4-(1,1,3,3-Tetramethylbutyl)phenyl-polyethylene glycol), Span® 80 (sorbitane monooleate), sorbitan monooleate, sorbitan monostearate, polyoxyethylemesorbitan monooleate, and octylphenoxyethoxyethanol. Ionic surfactants such as sodium cholate, sodium taurocholate, and sodium deoxycholate may also be used as emulsifying agents. Additional examples of emulsifying agents include chemically inert silicone-based surfactants such as polysiloxane-polycetyl-polyethylene glycol copolymer; fluorosurfactants such as perfluorinated polyethers (PFPE) and PFPE-PEG co-polymers; and cholesterol. Non-limiting examples of blocking proteins include serum albumins, such as bovine serum albumin and acetylated bovine serum albumin.

In certain embodiments, the emulsion is prepared such that various reagents or analytes are contained within the droplets of the emulsion. In certain embodiments, certain analytes or reagents may be attached to a solid support that also is disposed within the droplet. For example, probes and/or primers may be attached to a solid support. Such solid supports may be, for example, microspheres (e.g., beads) or other particles such as microparticles, gold or other metal nanoparticles, quantum dots, or nanodots. In certain aspects, the particles may be magnetic, paramagnetic, or super paramagnetic. Examples of microspheres, beads, and particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference herein.

Droplet Imaging

In exemplary embodiments, the droplets may be imaged by a variety of techniques. To facilitate imaging, the composition containing the droplets may be dispersed on a surface such that the droplets are disposed substantially in a monolayer on the surface. The imaging surface may be, for example, on a slide or in a chamber, such as a glass, plastic, or quartz chamber. The droplets, as well as labeled analytes or reaction products within the droplets, may be detected using an imaging system. For example, detecting labeled amplification products may comprise imaging fluorescent wavelengths and/or fluorescent intensities emitted from the labeled amplification products. In embodiments where the droplets contain encoded particles, such as encoded microspheres, the imaging may comprise taking a decoding image of the encoded particles and taking an assay image to detect amplification products in the droplets. A comparison of the decoding image and the assay image permits greater multiplex capabilities by using combinations of fluorophores. The methods of the present invention may further comprise correlating the signal from the directly or indirectly labeled amplification product with the concentration of DNA or RNA in a sample. Examples of imaging systems that could be adapted for use with the methods and compositions disclosed herein are described in U.S. Pat. No. 8,296,088 and U.S. Pat. Publ. 2012/0288897, which are incorporated herein by reference.

The droplets may be illuminated with any suitable light source. The light source may be configured to provide widespread illumination (i.e., illumination provided over all or a relatively large area of the imaging region simultaneously) using light emitted by light sources such as light emitting diodes (LEDs) or lasers and delivered to the imaging region directly or via an optical waveguide. Alternatively, the illumination source may be configured to provide illumination of a relatively small spot in the imaging region, and the system may be configured to scan the relatively small spot across the imaging region. In this manner, the illumination may be configured as a relatively "tiny flying spot" of focused light generated from one or more LED's, one or more lasers, one or more other suitable light sources, or some combination thereof. Imaging the illuminated droplets may comprise detecting light emitted or reflected from the imaging region of the chamber with a photosensitive detector. Non-limiting examples of photosensitive detectors include a photomultiplier tube (PMT), avalanche photo diode, CCD, CMOS or Quantum Dot camera.

The droplets may comprise labeling agents including, but not limited to, fluorophores, quantum dots, rare earth metals, and chemiluminescent compounds. The labeling agents may be free floating, attached to an analyte, attached to a reagent (e.g., a primer, probe, or antibody), attached to a magnetic particle, or any combination thereof. In certain embodiments, the labeling agent is one or more labeled primers or a dsDNA-binding dye. In one embodiment, the one or more labeled primers comprise a fluorophore/quencher pair or a FRET pair.

An imaging chamber may be composed of a single type of material or multiple materials. In some embodiments, at least a portion of the imaging chamber includes an optically clear material (such as, but not limited, to optically clear glass, plastic, or quartz), particularly in the vicinity of the imaging region such that an illumination beam may pass through the imaging chamber to image droplets in the imaging region. In some cases, a back portion of the imaging chamber corresponding to at least the imaging region may be configured to provide negligible reflectance and transmittance with respect to wavelengths of light emitted by the illumination system.

Assays

Numerous types of assays on a wide range of analytes may be performed inside of droplets. The analyte disposed within a droplet may be any analyte of interest including, without limitation, nucleic acids (including DNA or RNA), proteins (including enzymes or antibodies), hormones, carbohydrates, and cells. Depending on the type of analyte that is being detected, amplified, evaluated, etc., additional components may be disposed in the droplet. For example, where the analyte is a target nucleic acid, the aqueous droplets may further comprise one or more PCR reagents, such as primers, polymerase, $MgCl_2$, buffer, labeling agent, and/or dNTPs. In one embodiment, one species of primer is attached to a solid support disposed within the droplet. The solid support may be, for example, a microsphere or nanosphere. As a further example, where the analyte is a protein the aqueous droplets may further comprise one or more of an antibody, an enzyme, an enzyme substrate, a labeling agent, and/or BSA. To facilitate detection, analytes or reaction products may be directly or indirectly labeled with a labeling agent such as fluorophores, quantum dots, rare earth metals, and chemiluminescent compounds. The labeling agents may be free floating, attached to an analyte, attached to a reagent (e.g., a primer, probe, or antibody), attached to a magnetic particle, or any combination thereof. In certain embodiments, the labeling agent is one or more labeled primers or a dsDNA-binding dye. In one embodiment, the one or more labeled primers comprise a fluorophore/quencher pair or a FRET pair. In some embodiments, the labeling agent comprises a streptavidin-conjugated enzyme and a fluorogenic substrate. In one embodiment, the streptavidin-conjugated enzyme is a streptavidin-conjugated beta-galactosidase and the fluorogenic substrate is a resorufin beta-D-galactopyranoside.

The polymerase chain reaction (PCR) is an example of a reaction that may be performed within a droplet. In particular, droplets are useful in digital PCR (dPCR) techniques. dPCR involves partitioning the sample such that individual nucleic acid molecules contained in the sample are localized in many separate regions, such as in individual wells in microwell plates, in the dispersed phase of an emulsion, or arrays of nucleic acid binding surfaces. Each partition (e.g., droplet) will contain 0 or greater than zero molecules, providing a negative or positive reaction, respectively. Unlike conventional PCR, dPCR is not dependent on the number of amplification cycles to determine the initial amount of the target nucleic acid in the sample. Accordingly, dPCR eliminates the reliance on exponential data to quantify target nucleic acids and provides absolute quantification. Bead emulsion PCR, which clonally amplifies nucleic acids on beads in an emulsion, is one example of a dPCR technique in which the reactions are portioned into droplets. See, e.g., U.S. Pat. Nos. 8,048,627 and 7,842,457, which are hereby incorporated by reference. When dPCR is performed in an emulsion as discussed in more detail below, the emulsion should be heat stable to allow it to withstand thermal cycling conditions.

There are various ways of performing dPCR in an emulsion. For example, in one approach a DNA sample is diluted to an appropriate concentration, mixed with PCR reagents (primers, dNTPs, etc.) and encapsulated in droplets in an emulsion as described above, resulting in a number of discrete reaction samples. The droplets are subjected to PCR thermal cycling and the amplicons detected by florescence (or other suitable reporter) imaging as described above.

In another approach, an encoded microsphere is also contained in the droplet. The microsphere may be used to anchor a primer. By anchoring different primers to different encoded microspheres, each different primer, and the corresponding amplicon, may be identified by the encoded microsphere to which it is attached. An example of bead emulsion PCR is described in U.S. Pat. No. 8,048,627, which is incorporated herein by reference. It should be noted, however, that the technique described in the '627 patent involves breaking the emulsions and then isolating beads with a magnet in order to analyze the sequences on the beads. In contrast, amplicons may be detected within droplets (e.g., without having to break the emulsion) using the methods and composition described in the present disclosure.

The thermal cycling of the droplets may be performed by any suitable technique known in the art. For example, the droplets may be thermal cycled in a tube or chamber than can be heated and cooled. In some embodiments, the methods employ continuous-flow amplification to amplify the nucleic acid template. Various methods of continuous flow amplification have been reported. For example, U.S. Pat. No. 7,927,797, which in incorporated herein by reference, describes a water-in-oil emulsion used in conjunction with a continuous flow PCR. Continuous flow of the emulsion across a heat transfer element permits efficient and rapid reaction cycles and can be used for thermal amplification reactions (e.g., PCR) or isothermal reactions (e.g., rolling circle amplification, whole genome amplification, NASBA, or strand displacement amplification). In certain embodiments, the emulsion is flowed directly into the imaging region following continuous-flow amplification.

Single-molecule immunoassays and enzymatic assays may also be performed in droplets (see, e.g., Sakakihara et al., "A single-molecule enzymatic assay in a directly accessible femtoliter droplet array," Lab on a Chip 10:3355-3362 (2010); Sista et al., "Heterogeneous Immunoassays Using Magnetic Beads On a Digital Microfluidic Platform," Lab Chip. 8(12):2188-2196 (2008)).

WORKING EXAMPLES

In a first working example of an exemplary embodiment according to the present disclosure, droplets were generated using an emulsification device with a single multi-step nozzle having the following dimensions: CH=20 um, CW=60 um, SH1/CH=1.5 SH2/CH=1.75. The surfaces of the multi-step channel were coated with hydrophobic perfluorodecyltrichlorosilane (FDTS). In this example, a chemically inert oil (Fluorinert® FC-40) mixed with surfactant (to stabilize the droplets; PFPE-PEG-PFPE) was placed in the device. A 2 µM solution of oligonucleotides coupled to AP559 fluorescent dye in water was directed into the inlet portion of the multi-step channel at a flow rate of 1-100 nL/s. Droplets with a diameter of approximately 120 microns were formed, at a generation rate of 1 to 30 droplets per second and an average dispersion percentage of approximately 3.8 percent.

In a second working example of an exemplary embodiment according to the present disclosure, an emulsification device with 99 nozzles was used to produce droplets at a generation rate of approximately 20,000 droplets per minute. In this example, the average diameter of the droplets was approximately 122 microns, and the dispersion rate was approximately 9 percent. It is believed that the dispersion rate in this example was higher than expected due to a single, defective nozzle that produced inconsistent droplets. These nozzles were the same geometry used on the single nozzle part, CH=20 um, CW=60 um, SH1/CH=1.5, SH2/CH=1.75, droplet production rate of 1-30 droplets per nozzle per second. The continuous phase fluid was a solution of surfactant (PFPE-PEG-PFPE) in FC-40 and the dispersed phase was a 2 uM solution of oligonucleotides coupled to AP559 fluorescent dye in water.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiment of the present devices is not intended to be limited to the particular forms disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

The following references are incorporated herein by reference:
Sugiura, "Interfacial Tension Driven Monodispersed Droplet Formation from Microfabricated Channel Array", Langmuir 2001, 17, 5562-5566.
Dangla, "Droplet microfluidics driven by gradients of confinement", PNAS; Jan. 15, 2013; vol. 110, no. 3, 853-858.
U.S. Pat. No. 5,736,330
U.S. Pat. No. 5,981,180
U.S. Pat. No. 6,057,107
U.S. Pat. No. 6,268,222
U.S. Pat. No. 6,449,562
U.S. Pat. No. 6,514,295
U.S. Pat. No. 6,524,793
U.S. Pat. No. 6,528,165
U.S. Pat. No. 7,842,457
U.S. Pat. No. 7,927,797
U.S. Pat. No. 8,048,627
U.S. Pat. No. 8,296,088
U.S. Patent Pub. 2013/0078164
U.S. Pat. Publ. 2012/0288897

We claim:

1. A device for forming droplets, the device comprising:
a fluid supply channel;
a collection chamber; and
one or more nozzles disposed between and fluidically connected to the fluid supply channel and the collection chamber, wherein: each nozzle of the one or more nozzles comprises:
an inlet portion;
a first step; and
a second step, wherein the first step is disposed between and fluidically connected to the inlet portion and the second step;
the inlet portion has a channel height;
the first step has a first step height and a first tread length;
the first step height is greater than the channel height;
the second step has a second step height and a second tread length; and
the second step height is greater than the first step height.

2. The device of claim 1 wherein the first tread length is greater than the second tread length.

3. The device of claim 1 wherein:
the fluid supply channel is a first supply channel;
the collection chamber is a first collection chamber;
the one or more nozzles is a first one or more nozzles;
the device comprises a second fluid supply channel;
the device comprises a second collection chamber; and
the device comprises a second one or more nozzles disposed between and fluidically connected to the second fluid supply channel and the second collection chamber.

4. The device of claim 3 wherein:
the first collection chamber has a first collection chamber height;
the second collection chamber has a second collection chamber height; and
the first collection chamber height is different than the second collection chamber height.

5. The device of claim 3 wherein:
each nozzle of the second one or more nozzles comprises:
a second nozzle inlet portion;
a second nozzle first step; and
a second nozzle second step;
wherein the second nozzle first step is disposed between and fluidically connected to the second nozzle inlet portion and the second nozzle second step;
the second nozzle inlet portion has a second nozzle channel height;
the second nozzle first step has a second nozzle first step height and a second nozzle first tread length;
the second nozzle first step height is greater than the second nozzle channel height;
the second nozzle second step has a second nozzle second step height and a second nozzle second tread length; and
the second nozzle second step height is greater than the second nozzle first step height.

6. The device of claim 5 wherein the second nozzle first tread length is greater than the second nozzle second tread length.

7. The device of claim 5 wherein:
the first one or more nozzles comprise a first inlet portion having a first channel height configured to form droplets having a first diameter; and
the second one or more nozzles comprise a second inlet portion having a second channel height configured to form droplets having a second diameter that is greater than the first diameter.

8. The device of claim 7 wherein:
the first diameter is between 10 μm and 50 μm; and
the second diameter is between 80 μm and 300 μm.

9. The device of claim 5 where the second nozzle first step height is at least fifty percent greater than the first nozzle first step height.

10. The device of claim 5 where the second nozzle first step height is at least one hundred percent greater than the first nozzle first step height.

11. The device of claim 5 wherein the second nozzle second step height is at least fifty percent greater than the first nozzle second step height.

12. The device of claim 5 wherein the second nozzle second step height is at least one hundred percent greater than the first nozzle second step height.

13. The device of claim 1 wherein:
the inlet portion has a channel width;
the first step has a first step width; and
the first step width is greater than the channel width.

14. The device of claim 13 wherein:
the second step has a second step width; and
the second step width is greater than or equal to the first step width.

15. The device of claim 1 wherein:
the device comprises a first fluid and a second fluid; and
the first fluid is immiscible with the second fluid.

16. The device of claim 1 wherein a ratio of the first step height to the channel height is less than 2.

17. A method of forming droplets, the method comprising:
obtaining a device according to claim 1;
introducing a first fluid from the fluid supply channel into the one or more nozzles; and
forming a droplet from the first fluid in the one or more nozzles, wherein:
the droplet has a droplet length and a droplet height; and
the droplet is compressed in the one or more nozzles such that the droplet length is greater than the droplet height; and
collecting the droplet in the droplet collection chamber, wherein:
the droplet collection chamber contains a substantially static second fluid that is immiscible with the first fluid; and
the droplet is not compressed in the collection chamber such that the droplet length is equal to the droplet height.

18. The method of claim 17 wherein droplets are formed at a rate of between 10 and 30 complete droplets per second per nozzle.

19. The method of claim 17 wherein the droplet length is greater than the first tread length.

20. The method of claim 17 wherein the droplet length is less than the first tread length.

* * * * *